(12) United States Patent
Kurono et al.

(10) Patent No.: US 12,247,993 B2
(45) Date of Patent: Mar. 11, 2025

(54) SPECIMEN PLATELET AGGREGATION MEASUREMENT METHOD AND SPECIMEN PLATELET AGGREGATION MEASUREMENT APPARATUS

(71) Applicant: SYSMEX CORPORATION, Kobe (JP)

(72) Inventors: Hiroshi Kurono, Kobe (JP); Tasuku Sakayori, Kobe (JP); Yuri Watanabe, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 283 days.

(21) Appl. No.: 16/876,491

(22) Filed: May 18, 2020

(65) Prior Publication Data
US 2020/0400702 A1 Dec. 24, 2020

(30) Foreign Application Priority Data
Jun. 18, 2019 (JP) ................... 2019-112806

(51) Int. Cl.
*G01N 35/10* (2006.01)
*G01N 15/14* (2006.01)
(Continued)

(52) U.S. Cl.
CPC ......... *G01N 35/1016* (2013.01); *G01N 15/14* (2013.01); *G01N 33/487* (2013.01);
(Continued)

(58) Field of Classification Search
CPC .. G01N 35/1016; G01N 33/487; G01N 21/82; G01N 33/4905; G01N 15/14;
(Continued)

(56) References Cited

U.S. PATENT DOCUMENTS

| 4,808,380 A | * | 2/1989 | Minekane | ............ G01N 35/025 |
| | | | | 422/562 |
| 4,906,433 A | * | 3/1990 | Minekane | ............ G01N 35/025 |
| | | | | 422/561 |

(Continued)

FOREIGN PATENT DOCUMENTS

| CN | 101520465 A | 9/2009 |
| CN | 101520465 B | 7/2013 |

(Continued)

OTHER PUBLICATIONS

Mani, H. et al, Journal of Clinical Pathology 2005, 58, 747-750.*
(Continued)

*Primary Examiner* — Arlen Soderquist
(74) *Attorney, Agent, or Firm* — BUCHANAN INGERSOLL & ROONEY PC

(57) ABSTRACT

Disclosed is a specimen measurement method for measuring platelet aggregation of a specimen, and the specimen measurement method includes: automatically preparing a diluted reagent solution that contains a platelet-aggregating reagent diluted with a diluent; preparing a measurement sample that contains a predetermined concentration of the platelet-aggregating reagent, from the diluted reagent solution and the specimen; and performing optical measurement of the measurement sample.

20 Claims, 23 Drawing Sheets

(51) Int. Cl.
    *G01N 33/487* (2006.01)
    *G01N 15/01* (2024.01)

(52) U.S. Cl.
    CPC ............... *G01N 2015/018* (2024.01); *G01N 2035/1032* (2013.01)

(58) Field of Classification Search
    CPC .......... G01N 35/1002; G01N 35/1009; G01N 2035/00465; G01N 2035/0444; G01N 35/00584; G01N 35/00663; G01N 2035/00673; G01N 35/0092; G01N 2035/1032
    USPC .......................... 436/180, 43–55; 422/63–67
    See application file for complete search history.

(56) References Cited

U.S. PATENT DOCUMENTS

| | | | | |
|---|---|---|---|---|
| 5,355,304 | A | * | 10/1994 | DeMoranville ........ G16H 10/60 700/245 |
| 5,563,041 | A | * | 10/1996 | Reers ..................... G01N 33/86 530/382 |
| 5,597,733 | A | * | 1/1997 | Bell ..................... G01N 35/1004 422/561 |
| 6,090,630 | A | * | 7/2000 | Koakutsu ......... G01N 35/00732 422/63 |
| 2001/0024803 | A1 | | 9/2001 | Patzke |
| 2005/0013738 | A1 | * | 1/2005 | Schwalbe ............ G05B 13/024 422/67 |
| 2006/0004530 | A1 | * | 1/2006 | Miyamoto ....... G01N 35/00584 702/30 |
| 2007/0212261 | A1 | * | 9/2007 | Tanaka ..................... G01F 23/56 422/67 |
| 2008/0044912 | A1 | * | 2/2008 | Yamamoto ............. G01N 21/82 436/69 |
| 2009/0004681 | A1 | * | 1/2009 | Hoshiko ............ G01N 33/4905 435/13 |
| 2009/0214385 | A1 | * | 8/2009 | Mori ................ G01N 35/00663 422/63 |
| 2010/0114501 | A1 | * | 5/2010 | Kondou .................. B01L 3/527 702/22 |
| 2010/0161243 | A1 | * | 6/2010 | Nagai .............. G01N 35/00663 702/25 |
| 2010/0191382 | A1 | * | 7/2010 | Samuhel ................ G05B 15/02 700/285 |
| 2010/0247379 | A1 | * | 9/2010 | Schmidt ................. G05D 21/02 422/77 |
| 2010/0248289 | A1 | * | 9/2010 | Asahara ........... G01N 35/00663 422/63 |
| 2011/0312015 | A1 | * | 12/2011 | Velaskar ................ G01N 33/86 435/29 |
| 2012/0237400 | A1 | * | 9/2012 | Ikeda ............... G01N 35/00663 422/68.1 |
| 2013/0203175 | A1 | * | 8/2013 | Xu .................... A61B 5/150755 436/63 |
| 2015/0198620 | A1 | | 7/2015 | Trolio |
| 2015/0276769 | A1 | | 10/2015 | Yamaguchi et al. |
| 2015/0309060 | A1 | | 10/2015 | Tamagawa et al. |
| 2016/0187360 | A1 | * | 6/2016 | Shikata ..................... B01L 9/06 422/549 |
| 2016/0238624 | A1 | * | 8/2016 | Morishima ........ G01N 35/1002 |
| 2016/0282377 | A1 | | 9/2016 | Nagai et al. |
| 2016/0299164 | A1 | * | 10/2016 | Ackermann ..... G01N 35/00693 |
| 2018/0259545 | A1 | | 9/2018 | Katsumi et al. |
| 2018/0267069 | A1 | * | 9/2018 | Katsumi ............ G01N 35/1002 |
| 2018/0327120 | A1 | * | 11/2018 | Turzi ................... A61K 31/722 |
| 2020/0209218 | A1 | * | 7/2020 | Ye ......................... G01N 33/49 |

FOREIGN PATENT DOCUMENTS

| | | |
|---|---|---|
| CN | 104020302 A | 9/2014 |
| CN | 104949930 A | 9/2015 |
| CN | 105637369 A | 6/2016 |
| CN | 108291923 A | 7/2018 |
| EP | 2 187 219 A1 | 5/2010 |
| JP | S57-000552 A | 1/1982 |
| JP | S58-095261 A | 6/1983 |
| JP | S62-228952 A | 10/1987 |
| JP | H03-4168 A | 1/1991 |
| JP | 04106472 A * | 4/1992 |
| JP | 04265140 A * | 9/1992 |
| JP | H0810226 B2 | 1/1996 |
| JP | 2005017254 A | 1/2005 |
| WO | 2014/025968 A2 | 2/2014 |

OTHER PUBLICATIONS

Linnemann, B. et al, Journal of Thrombosis and Haemostasis 2008, 6, 677-683.*
Hayward, C. P. M. et al, Thrombosis and Haemostasis 2008, 100, 12 pages.*
Lawrie, A. S. et al, International Journal of Laboratory Hematology 2014, 36, 431-438.*
Zucker, M. B., Methods in Enzymology 1989, 169, 117-133.*
Bednar, B. et al, Thrombosis Research 1995, 77, 453-463.*
Craft, R. M. et al, Journal of Laboratory and Clinical Medicine 2004, 143, 301-309.*
Dyszkiewicz-Korpanty, A. M. et al, Clinical and Applied Thrombosis/Hemostasis 2005, 11, 25-35.*
Zhou, L. et al, American Journal of Clinical Pathology 2005, 123, 172-183.*
Beyan, C. et al, Journal of Thrombosis and Thrombolysis 2006, 22, 161-164.*
Cattaneo, M. et al, Haematologica 2007, 92, 694-697.*
Chan, M. V. et al, Platelets 2011, 22, 485-494.*
Femia, E. A. et al, Platelets 2012, 23, 7-10.*
Soderstrom, A, C. et al, Clinical Chemistry and Laboratory Medicine 2016, 54, 1913-1920.*
Fratantoni, J. C. et al, American Journal of ClinicalPathology 1990, 94, 613-617. (Year: 1990).*
Arai, N. et al, Sysmex Journal International 2007, 17, Supplement 1, 49-59. (Year: 2007).*
Extended European Search Report issued on Nov. 10, 2020, by the European Patent Office in corresponding European Patent Application No. 20180223.8-1118. (10 pages).
Cattaneo et al., "Results of a Worldwide Survey on the Assessment of Platelet Function by Light Transmission Aggregometry: a Report from the Platelet Physiology Subcommittee of the Scientific and Standardization Committee of the International Society on Thrombosis and Haemostasis", Journal of Thrombosis and Haemostasis, (Posted on Website May 1, 2009), vol. 7, No. 6, (26 pages).
Harrison et al., "Guidelines for the Laboratory Investigation of Heritable Disorders of Platelet Function", British Journal of Haematology, (2011), vol. 155, No. 1, pp. 30-44, Blackwell Publishing Ltd.
Tomiyama et al., "Introduction and commentary of "Standardization of transmitted light platelet condensation test: Recommendations from the International Society for Thrombosis and Hemostasis, Platelet Standardization Committee"", Japanese Journal of Thrombosis and Hemostasis, The Japanese Society on Thrombosis and Hemostasis, (2016), vol. 27, No. 3, pp. 365-369, and an English translation thereof.
Office Action (Notification of Reasons for Refusal) issued on Jan. 31, 2020, by the Japanese Patent Office in corresponding Japanese Patent Application No. 2019-112806 and an English Translation of the Office Action. (20 pages).
Office Action (Notification of Reasons for Refusal) issued on May 18, 2020, by the Japanese Patent Office in corresponding Japanese Patent Application No. 2019-112806 and an English Translation of the Office Action. (7 pages).
Decision of Refusal issued on Apr. 24, 2023, by the Japanese Patent Office in counterpart Japanese Patent Application No. 2020-157091, and an English translation of the Decision (5 pgs).
Kimura, M. et al., "Platelet aggregation test using automated coagulation analyzer CS-21001: Evaluation of basic performance and efficacy assessment of antiplatelet drugs", Japanese Journal of

(56) References Cited

OTHER PUBLICATIONS

Medical Technology (Igakukensa), 2017, Japanese Association of Medical Technologists, vol. 66, No. 5, pp. 471-477, (16 pages).

Matsuno, K. et al., "Relationship between platelet counts in platelet rich plasma and platelet aggregation", Blood & Vessel, 1978, The Japanese Society on Thrombosis and Hemostasis, vol. 9, No. 3, pp. 371-374, (9 pages).

Office Action (Notice of Reasons for Refusal) issued on Jan. 4, 2023, by the Japanese Patent Office in corresponding Japanese Patent Application No. 2020-157091, and an English translation of the Office Action. (9 pages).

Office Action (The First Office Action) issued on Jan. 18, 2024, by the National Intellectual Property Administration, PRC in corresponding Chinese Patent Application No. 202010347840.0, and an English Translation of the Office Action. (28 pages).

Office Action (Notice of Second Office Action) issued on Sep. 26, 2024, by the State Intellectual Property Office in corresponding Chinese Patent Application No. 202010347840.0, and an English Translation of the Office Action. (40 pages).

\* cited by examiner

FIG. 11

| REAGENT DILUTION | ①INPUT TEST NUMBER | ②REAGENT PREPARATION | ③CONFIRM EXECUTION OF DILUTION | ④EXECUTION RESULT |

INDUCER IS PRODUCED.
INPUT TEST NUMBER TO BE PRODUCED AND PRESS "TO-THE-NEXT" BUTTON.

UNDILUTED SOLUTION/DILUENT:

| NAME OF REAGENT | FINAL CONCENTRATION | REQUIRED AMOUNT [μL] |
|---|---|---|
| ADP | 160.0 uM | 580 |
| Col | 800.0 ug/mL | 339 |
| Ara | 12.0 mM | 0 |
| Epi | 800.0 uM | 340 |
| Ris | 12.0 mg/mL | 0 |
| Saline | - | 1520 |
| Col.Dil | - | 1702 |

REAGENT TO BE PRODUCED:

| NAME OF REAGENT | FINAL CONCENTRATION | TEST NUMBER (TO BE PRODUCED) |
|---|---|---|
| ADP1.0 | 1.0 uM | 15 |
| ADP2.0 | 2.0 uM | 10 |
| ADP10.0 | 10.0 uM | 5 |
| Col1.0 | 1.0 ug/mL | 12 |
| Col2.0 | 2.0 ug/mL | 5 |
| Ara1.0 | 1.0 mM | |
| Epi5.0 | 5.0 uM | 25 |
| Ris1.2 | 1.0 mg/mL | |

— 702
— 703
— 802

[PRESETTING STORING] 704
[PRESETTING READING] 705
[CALCULATE REQUIRED AMOUNT] 706

[CANCEL] [TO THE NEXT]

FIG. 13

REAGENT DILUTION

①INPUT TEST NUMBER 〉 ②REAGENT PREPARATION 〉 ③CONFIRM EXECUTION OF DILUTION 〉 ④EXECUTION RESULT

SET UNDILUTED SOLUTION, DILUENT, AND REAGENT TO BE PRODUCED, AND MEASURE REMAINING AMOUNT.
PRESS "RETURN" BUTTON WHEN GENERATED CONTENTS ARE TO BE CORRECTED, AND PRESS "TO-THE-NEXT" BUTTON AFTER REGENT HAS BEEN PREPARED.

UNDILUTED SOLUTION: ▲5 707
DILUENT:

| NAME OF REAGENT | FINAL CONCENTRATION | REQUIRED AMOUNT [μL] | CURRENT AMOUNT [μL] | POSITION FOR SETTING |
|---|---|---|---|---|
| ADP | 160.0uM | 580 | ▲ | |
| Col | 800.0 ug/mL | 339 | ▲ | |
| Ara | 12.0 mM | 0 | ▲ | |
| Epi | 800.0 uM | 340 | ▲ | |
| Ris | 12.0 mg/mL | 0 | ▲ | |
| Saline | - | 1520 | ▲ | |
| Col.Dil | - | 1702 | ▲ | |

708

REAGENT TO BE PRODUCED: ▲8

| NAME OF REAGENT | FINAL CONCENTRATION | REQUIRED AMOUNT [μL] | CURRENT AMOUNT [μL] | POSITION FOR PRODUCTION |
|---|---|---|---|---|
| ADP1.0 | 1.0uM | 600 | ▲ | |
| ADP2.0 | 2.0uM | 500 | ▲ | |
| ADP10.0 | 10.0uM | 400 | ▲ | |
| Col1.0 | 1.0 ug/mL | 540 | ▲ | |
| Col2.0 | 2.0 ug/mL | 400 | ▲ | |
| Ara1.0 | 1.0 mM | 500 | ▲ | |
| Epi5.0 | 5.0 uM | 800 | ▲ | |
| Ris1.2 | 1.0 mg/mL | 500 | ▲ | |

[MEASURE REMAINING AMOUNT] 709   [RETURN]   [TO THE NEXT]   [CANCEL]

REAGENT DILUTION

①INPUT TEST NUMBER  ②REAGENT PREPARATION  ③CONFIRM EXECUTION OF DILUTION  ④EXECUTION RESULT

SET UNDILUTED SOLUTION, DILUENT, AND REAGENT TO BE PRODUCED, AND MEASURE REMAINING AMOUNT.
PRESS "RETURN" BUTTON WHEN GENERATED CONTENTS ARE TO BE CORRECTED, AND PRESS "TO-THE-NEXT" BUTTON AFTER REGENT HAS BEEN PREPARED.

UNDILUTED SOLUTION/ ▲5
DILUENT:

| NAME OF REAGENT | FINAL CONCENTRATION | AM... | [μL] | CURRENT AMOUNT [μL] | POSITION FOR PRODUCTION |
|---|---|---|---|---|---|
| ADP | 160.0 uM | | 600 | ▲ | |
| Col | 800.0 ug/mL | | 500 | ▲ | |
| Ara | 12.0 mM | | 400 | ▲ | |
| Epi | 800.0 uM | | 540 | ▲ | |
| Ris | 12.0 mg/mL | | 400 | ▲ | |
| Saline | | | 500 | ▲ | |
| Col.Dil | | 1702 | 800 | ▲ | |
| | Epi 5.0 | 5.0 uM | | 500 | ▲ |
| | Ris 1.2 | 1.0 mg/mL | | | |

BARCODE READING

REPLACEMENT OF REAGENT IS ENDED AND REAGENT INFORMATION IS READ. PRESS [CANCEL] BUTTON WHEN REPLACEMENT OF REAGENT IS CONTINUED.

☐ MEASURE REMAINING AMOUNT OF REAGENT AFTER BARCODE HAS BEEN READ

CLOSE OPERATION COVER WHEN REMAINING AMOUNT OF REAGENT IS MEASURED AFTER BARCODE HAS BEEN READ.

[ OK ]  [ CANCEL ]

[ MEASURE REMAINING AMOUNT ]  [ RETURN ]  [ TO THE NEXT ]  [ CANCEL ]

REAGENT DILUTION

| REAGENT DILUTION | ①INPUT TEST NUMBER | ②REAGENT PREPARATION | ③CONFIRM EXECUTION OF DILUTION | ④EXECUTION RESULT |

SET UNDILUTED SOLUTION, DILUENT AND REAGENT TO BE PRODUCED, AND MEASURE REMAINING AMOUNT. PRESS "RETURN" BUTTON WHEN GENERATED CONTENTS ARE TO BE CORRECTED, AND PRESS "TO-THE-NEXT" BUTTON AFTER REGENT HAS BEEN PREPARED.

UNDILUTED SOLUTION/DILUENT:

| NAME OF REAGENT | FINAL CONCENTRATION | REQUIRED AMOUNT [μL] | CURRENT AMOUNT [μL] | POSITION FOR SETTING |
|---|---|---|---|---|
| ADP | 160.0 uM | 580 | 600 | A1-1 |
| Col | 800.0 ug/mL | 339 | 350 | A1-3 |
| Epi | 800.0 uM | 340 | 350 | A1-5 |
| Saline | - | 1520 | 1600 | A1-7 |
| Col.Dil | - | 1702 | 1750 | A1-9 |

711

REAGENT TO BE PRODUCED:

| NAME OF REAGENT | FINAL CONCENTRATION | PRODUCED AMOUNT | CURRENT AMOUNT | POSITION FOR PRODUCTION |
|---|---|---|---|---|
| ADP1.0 | 1uM | 600 | 0 | A2-1 |
| ADP2.0 | 2uM | 500 | 500 | A2-3 |
| ADP10.0 | 10uM | 400 | 2800 | A2-5 |
| Col1.0 | 1 ug/mL | 540 | 0 | A2-7 |
| Col2.0 | 2 ug/mL | 400 | 0 | A2-9 |
| Col5.0 | 5 ug/mL | 500 | 0 | A3-3 |
| Epi5.0 | 5 uM | 800 | 0 | A3-5 |

804

| MEASURE REMAINING AMOUNT | RETURN | TO THE NEXT | CANCEL |

REAGENT DILUTION

| REAGENT DILUTION | ① INPUT TEST NUMBER | ② REAGENT PREPARATION | ③ CONFIRMATION OF DILUTION | ④ EXECUTION RESULT |

INDUCER IS PRODUCED ACCORDING TO THE FOLLOWING ORDER CONTENTS.
PRESS [EXECUTION] BUTTON AFTER CONFIRMATION.

| RESULT | NAME OF REAGENT | FINAL CONCENTRATION | TEST NUMBER TO BE PRODUCED | CURRENT AMOUNT [μL] | POSITION FOR PRODUCTION | ERROR |
|---|---|---|---|---|---|---|
| | ADP1.0 | 1.0 uM | 600 | 600 | A2-1 | |
| | ADP2.0 | 2.0 uM | 500 | 500 | A2-3 | |
| ⚠ | ADP10.0 | 10.0 uM | 400 | 400 | A2-5 | ERROR CONTENTS |
| | Col1.0 | 1.0 ug/mL | 540 | 540 | A2-5 | |
| | Col2.0 | 2.0 ug/mL | 400 | 400 | A2-7 | |
| | Ara1.0 | 1.0 mM | 500 | 500 | A3-3 | |
| | Epi5.0 | 5.0 uM | 800 | 800 | A3-3 | |
| | Ris1.2 | 1.0 mg/mL | 500 | 500 | A3-5 | |

CANCEL  EXECUTE

FIG. 20

REAGENT DILUTION

| REAGENT DILUTION | ① INPUT TEST NUMBER | ② REAGENT PREPARATION | ③ CONFIRM EXECUTION OF DILUTION | ④ EXECUTION RESULT |

THE FOLLOWING INDUCERS HAVE BEEN PRODUCED.

| RESULT | NAME OF REAGENT | FINAL CONCENTRATION | TEST NUMBER TO BE PRODUCED | CURRENT AMOUNT [μL] | POSITION FOR PRODUCTION | ERROR |
|---|---|---|---|---|---|---|
| ⊙ | ADP1.0 | 1.0 uM | 600 | 600 | A2-1 | |
| ⊙ | ADP2.0 | 2.0 uM | 500 | 500 | A2-3 | |
| ▲ | ADP10.0 | 10.0 uM | 400 | 400 | A2-5 | ERROR CONTENTS |
| ⊙ | Col1.0 | 1.0 ug/mL | 540 | 540 | A2-5 | |
| ⊙ | Col2.0 | 2.0 ug/mL | 400 | 400 | A2-7 | |
| ⊙ | Ara1.0 | 1.0 mM | 500 | 500 | A2-5 | |
| ⊙ | Epi5.0 | 5.0 uM | 800 | 800 | A3-3 | |
| ▲ | Ris1.2 | 1.0 mg/mL | 500 | 500 | A3-5 | ERROR CONTENTS |

CLOSE

SPECIMEN PLATELET AGGREGATION MEASUREMENT METHOD AND SPECIMEN PLATELET AGGREGATION MEASUREMENT APPARATUS

CROSS REFERENCE TO RELATED APPLICATIONS

This application claims priority from prior Japanese Patent Application No. 2019-112806, filed on Jun. 18, 2019, entitled "SPECIMEN MEASUREMENT METHOD AND SPECIMEN MEASUREMENT APPARATUS", the entire content of which is incorporated herein by reference.

FIELD OF THE INVENTION

The present invention relates to measurement technology, and specifically relates to a specimen measurement method and a specimen measurement apparatus.

BACKGROUND

A platelet aggregation test is useful for diagnosing a congenital disease such as thrombasthenia and Bernard-Soulier syndrome, discerning a pathological condition of a thrombotic disease of an arterial system such as myocardial infarction and cerebral infarction, detecting dysfunction of platelet aggregation in an antiplatelet therapy that is one of therapies for thrombotic diseases of an arterial system, and monitoring a drug efficacy of an antiplatelet aggregation drug (for example, see Japanese Examined Patent Publication No. 8-10226, and Japanese Laid-Open Patent Publication No. 2005-17254). For example, states of platelet aggregation of specimens are classified for each of a plurality of platelet aggregation inducers for inducing platelet aggregation, to specify a disease associated with congenital abnormality of platelets.

As described above, a plurality of kinds of platelet aggregation inducers for inducing platelet aggregation are used, and various concentrations are used for each inducer according to the purpose of the test, test facilities, and the like. Therefore, a wide variety of platelet aggregation test methods are used and the standardization is not promoted. Accordingly, in an apparatus for measuring platelet aggregation by measuring an absorbance of a specimen, preparation of an appropriate concentration of a platelet aggregation inducer is not automated, and is manually performed.

However, manual preparation of a plurality of kinds of platelet aggregation inducers at a plurality of concentrations is complicated, and a test efficiency of the platelet aggregation test is reduced. Furthermore, if a plurality of kinds of platelet aggregation inducers are manually prepared at a plurality of concentrations, the concentration may vary depending on a skill of an operator, so that the test accuracy may be degraded.

SUMMARY OF THE INVENTION

The scope of the present invention is defined solely by the appended claims, and is not affected to any degree by the statements within this summary.

According to one aspect of the present invention, as shown in FIG. 8, a specimen measurement method for measuring platelet aggregation of a specimen is provided, and the specimen measurement method includes: step S10 of automatically preparing a diluted reagent solution that contains a platelet-aggregating reagent diluted with a diluent; and S11 of preparing a measurement sample that contains a predetermined concentration of the platelet-aggregating reagent, from the diluted reagent solution and the specimen and performing optical measurement of the measurement sample.

In the specimen measurement method, a diluted reagent solution is automatically prepared, and, therefore, a load of preparation of the diluted reagent solution is reduced, and variation in concentration due to a skill of an operator is reduced.

According to another aspect of the present invention, as shown in FIG. 1, a specimen measurement apparatus 200 for measuring platelet aggregation of a specimen is provided, and the specimen measurement apparatus 200 includes: a diluted reagent solution preparation unit 11 configured to prepare a diluted reagent solution that contains a platelet-aggregating reagent diluted with a diluent; a measurement sample preparation unit 12 configured to prepare a measurement sample that contains a predetermined concentration of the platelet-aggregating reagent, from the diluted reagent solution and the specimen; and a measurement unit 13 configured to perform optical measurement of the measurement sample.

In the specimen measurement apparatus 200, a diluted reagent solution is automatically prepared, and, therefore, a load of preparation of the diluted reagent solution is reduced, and variation in concentration due to a skill of an operator is reduced.

The present invention can provide a specimen measurement method and a specimen measurement apparatus that reduce a load of preparation of a platelet-aggregating reagent and reduce variation in concentration due to a skill of an operator when platelet aggregation of the specimen is tested.

BRIEF DESCRIPTION OF THE DRAWINGS

FIG. 11 is a schematic diagram illustrating a screen representing a test number input screen according to the embodiment;

FIG. 13 is a schematic diagram illustrating a reagent preparation screen according to the embodiment;

FIG. 15 is a schematic diagram illustrating the reagent preparation screen and a dialog box according to the embodiment;

FIG. 16 is a schematic diagram illustrating the reagent preparation screen according to the embodiment;

FIG. 17 is a schematic diagram illustrating a dilution execution confirmation screen according to the embodiment;

FIG. 20 is a schematic diagram illustrating an execution result display screen according to the embodiment;

DETAILED DESCRIPTION OF THE PREFERRED EMBODIMENTS

Figure 1:
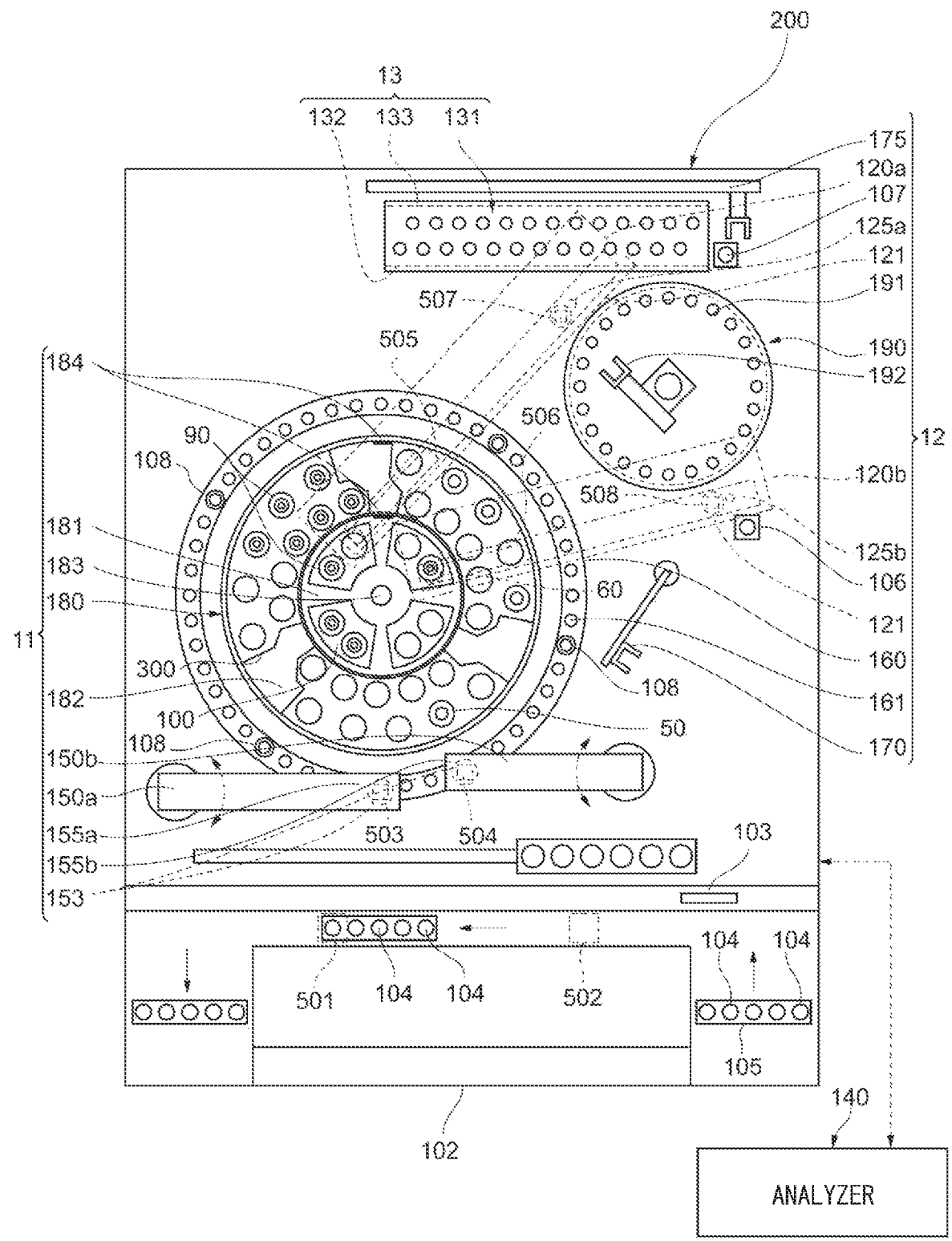
FIG. 1 is a schematic top view of a specimen measurement apparatus according to an embodiment.

An embodiment of the present disclosure will be described below with reference to the drawings. In the drawings, the same or similar components are denoted by the same or similar reference characters. However, the drawings are schematic. Therefore, specific dimensions and the like are to be determined with reference to the following description. It is needless to say that dimensional relationship and ratios may be different throughout the drawings.

As shown in FIG. 1, a specimen measurement apparatus 200, according to the embodiment, for measuring platelet aggregation of a specimen includes: a diluted reagent solution preparation unit 11 for automatically preparing a diluted reagent solution that contains a platelet-aggregating reagent diluted with a diluent; a measurement sample preparation unit 12 for preparing a measurement sample that contains a predetermined concentration of the platelet-aggregating reagent, from the diluted reagent solution and a specimen; and a measurement unit 13 for performing optical measurement of the measurement sample.

The platelet-aggregating reagent contains a platelet-aggregating substance (platelet aggregation inducer), and includes adenosine diphosphate (ADP), collagen, epinephrine, arachidonic acid, ristocetin, or protease-activated receptor 1-activating peptide (PAR1-AP). As ADP, Revohem (registered trademark, SYSMEX CORPORATION) ADP can be used. As the collagen, Revohem (registered trademark, SYSMEX CORPORATION) collagen can be used. As epinephrine, Revohem (registered trademark, SYSMEX CORPORATION) epinephrine can be used. As arachidonic acid, Revohem (registered trademark, SYSMEX CORPORATION) arachidonic acid can be used. As ristocetin, Revohem (registered trademark, SYSMEX CORPORATION) ristocetin can be used. In the present embodiment, a user dilutes powder of freeze-dried reagent with purified water in advance, to prepare solution containing the platelet-aggregating reagent.

As the diluent for diluting solution containing the platelet-aggregating reagent, saline or a diluent for collagen is used.

The diluted reagent solution preparation unit 11 includes a reagent preparation table 180. The reagent preparation table 180 is a round table. On the reagent preparation table 180, a plurality of container racks 100, 300 are disposed along the circumferential direction, and a reagent container 90 in which solution containing a reagent is stored by a user, a diluent container 50 for storing diluent, and an empty diluted reagent solution container 60 are disposed in the container racks 100, 300. The user places the reagent container 90, the diluent container 50, and the diluted reagent solution container 60 in the container racks 100, 300. The user also places the container racks 100, 300 on the reagent preparation table 180.

The reagent preparation table 180 includes a first table 181 that is disposed at the center portion and has a round shape in a planar view, and a second table 182 that is disposed on the outer circumference of the first table 181 and has an annular shape in a planar view. In the example shown in FIG. 1, the first table 181 has the four container racks 100 arranged along the circumferential direction. The second table 182 has the three large container racks 300 arranged along the circumferential direction.

The reagent preparation table 180 is rotatable in the circumferential direction, and can move, by its rotation, each of the reagent container 90, the diluent container 50, and the diluted reagent solution container 60 to a predetermined position. The first table 181 and the second table 182 are rotatable independently around a rotation shaft 183 in the circumferential direction by a rotation mechanism having an electric motor. The first table 181 can move, by its rotation, each of the reagent container 90, the diluent container 50, and the diluted reagent solution container 60 disposed in the first table 181 to a predetermined position. The second table 182 can move, by its rotation, each of the reagent container 90, the diluent container 50, and the diluted reagent solution container 60 disposed in the second table 182 to a predetermined position.

The reagent preparation table 180 may be covered by a case having a heat-insulating performance. The reagent preparation table 180 has a temperature adjusting unit such as a Peltier device. The reagent preparation table 180 functions as a reagent cooler for holding each of the reagent container 90, the diluent container 50, and the diluted reagent solution container 60 which are held in the container racks 100, 300 disposed therein, at a predetermined storage temperature.

Figure 2:
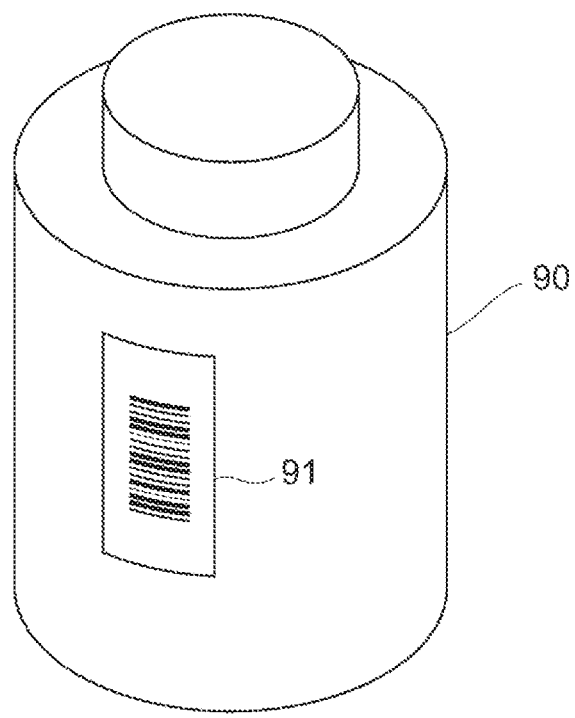
FIG. 2 is a schematic perspective view of a reagent container according to the embodiment.

The diluted reagent solution preparation unit 11 includes reagent information readers 184 for reading identification information allocated to each of the reagent container 90, the diluent container 50, the diluted reagent solution container 60, and the container racks 100, 300. As shown in FIG. 2, the identification information is allocated as a barcode 91, and the reagent information reader 184 shown in FIG. 1 includes a barcode reader. The identification information allocated to the reagent container 90 may include information such as a name of a reagent, a kind of the reagent, the concentration of the reagent in solution containing the reagent, a lot number, an expiration date, and an identification number (ID) of each reagent container 90. The identification information allocated to the diluent container 50 may include information such as a name of a diluent, a kind of the diluent, a lot number, an expiration date, and an identification number (ID) of each diluent container 50. The identification information allocated to the diluted reagent solution container 60 may include information such as an identification number (ID) of each diluted reagent solution container 60. The identification information allocated to the container racks 100, 300 may include information such as identification numbers (ID) of the container racks 100, 300, respectively.

Each of the first table 181 and the second table 182 can move the reagent container 90, the diluent container 50, the diluted reagent solution container 60, and the container racks 100, 300 which are disposed therein, to a reading position corresponding to the reagent information reader 184. The reagent information reader 184 reads identification information of each of the reagent container 90, the diluent container 50, the diluted reagent solution container 60, and the container racks 100, 300, thereby specifying positioning of the reagent container 90, the diluent container 50, and the diluted reagent solution container 60, respectively, in the reagent preparation table 180.

Figure 3:
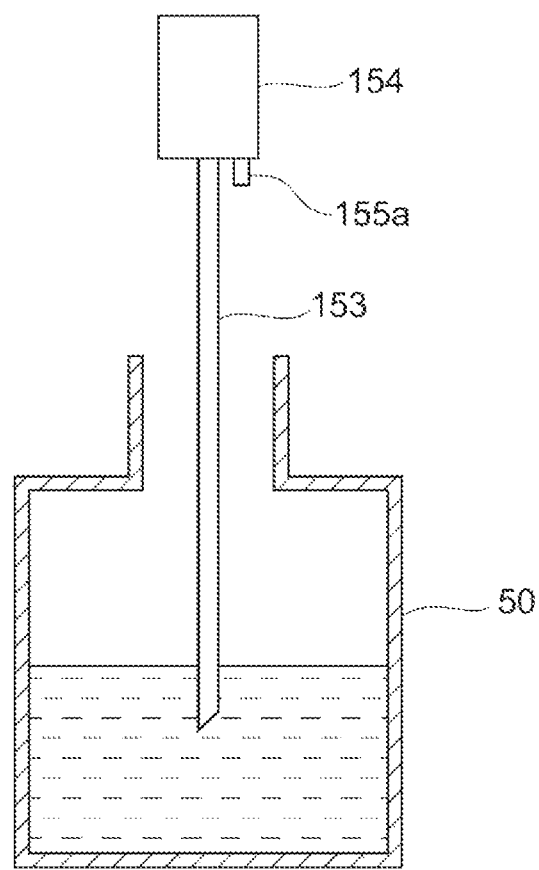
FIG. 3 is a schematic side view of a suction tube and a pump of a first dispenser according to the embodiment.

The diluted reagent solution preparation unit 11 includes first dispensers 150a, 150b. The first dispensers 150a, 150b each include a dispensing arm for holding a dispensing suction tube 153 such that the suction tube 153 is pivotable. As shown in FIG. 3, the suction tube 153 is connected to a pump 154, and can suction a predetermined amount of fluid and dispense the predetermined amount of fluid. Each of the first dispensers 150a, 150b shown in FIG. 1 moves the suction tube 153 onto the diluent container 50, and suctions a predetermined amount of a diluent from the diluent container 50, and dispenses the predetermined amount of the diluent into the diluted reagent solution container 60. Each of the first dispensers 150a, 150b moves the suction tube 153 onto the reagent container 90, and suctions a predetermined amount of a reagent from the reagent container 90, and dispenses the predetermined amount of the reagent into the diluted reagent solution container 60. Thus, the reagent and the diluent are mixed in the diluted reagent solution container 60, and the reagent is diluted with the diluent, to prepare a diluted reagent solution that contains the reagent.

The number of the first dispensers is not particularly limited, and may be one or plural.

The diluted reagent solution preparation unit 11 includes solution amount detectors 155a, 155b each of which detects a storage amount of solution stored in each of the reagent container 90, the diluent container 50, and the diluted reagent solution container 60. The solution amount detectors 155a, 155b each include a liquid level detection sensor for detecting the height of the liquid level of the solution stored in each of the reagent container 90, the diluent container 50, and the diluted reagent solution container 60. The solution amount detector 155a shown in FIG. 3 includes a capacitance-type liquid level detection sensor. The liquid level detection sensor senses contact of the lower end of the suction tube 153 with the liquid level of the solution. As shown in FIG. 1, the solution amount detectors 155a, 155b are disposed at the first dispensers 150a, 150b.

The specimen measurement apparatus 200 is connected to a transportation section 102 for transporting a specimen. A specimen rack 105 is disposed in the transportation section 102. In the specimen rack 105, a plurality of specimen containers 104 for storing specimens are disposed. The specimen is, for example, a platelet-rich plasma (PRP) specimen and a platelet-poor plasma (PPP) specimen. The PRP specimen is, for example, a supernatant obtained by centrifuging blood having an anticoagulant agent such as sodium citrate added thereto, at $200 \times_g$ for 10 minutes. ×g is a unit of a centrifugal force. The PPP specimen is, for example, a supernatant obtained by centrifuging blood having an anticoagulant agent such as sodium citrate added thereto, at 200×g for 10 minutes, and further centrifuging the obtained product at 1500×g for one minute. The specimen container 104 that stores the PRP specimen and the specimen container 104 that stores the PPP specimen are preferably paired and disposed in the specimen rack 105.

Figure 4A:
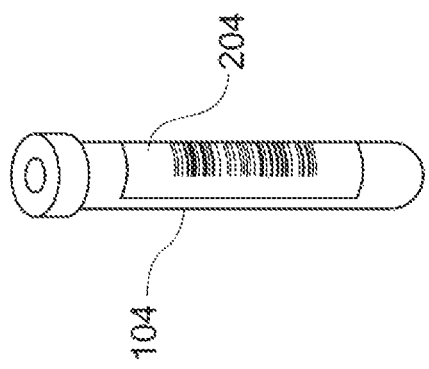
FIGS. 4A and 4B are a schematic side view of a specimen rack and a specimen container according to the embodiment.
Figure 4B:
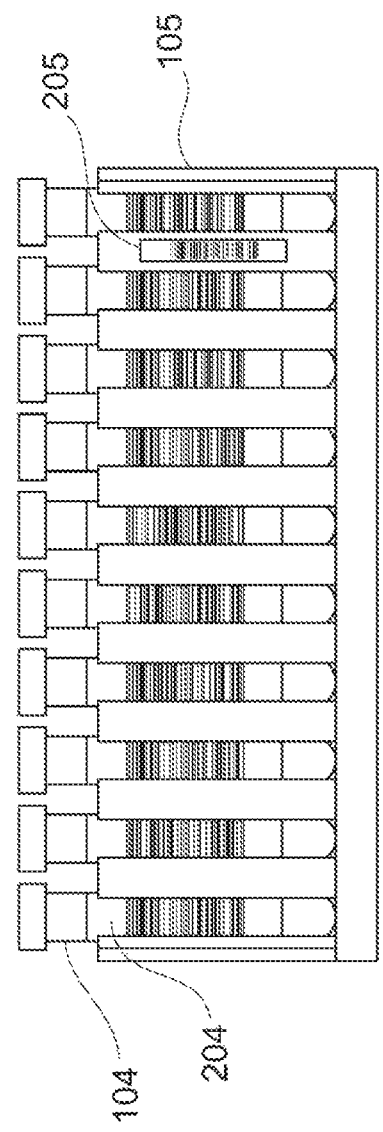

The transportation section 102 transports the specimen rack 105 placed by a user, to position each specimen container 104 at a predetermined specimen suctioning position 501, 502. As shown in FIGS. 4A and 4B, the specimen rack 105 and the specimen container 104 have labels 205, 204 which are adhered thereto and store identification information in a barcode or the like. The identification information includes information indicating whether the specimen contained in each of the specimen containers 104 is the PRP specimen or the PPP specimen. The identification information also includes information about, for example, a provider of the specimen contained in each of the specimen containers 104, and the purpose of testing the specimen. The transportation section 102 shown in FIG. 1 includes a specimen information reader 103 disposed in a transport route in which the specimen rack 105 and the specimen container 104 are transported. The specimen information reader 103 includes a barcode reader. The specimen information reader 103 reads the identification information of the specimen rack 105 and the specimen container 104, and transmits the identification information to an analyzer 140 described below. The identification information allows the specimen in the specimen container 104 and the measurement result obtained later to be associated with each other and managed.

Each of the first dispensers 150a, 150b can suction a predetermined amount of specimen in the specimen container 104, and dispense the predetermined amount of the specimen into a reaction container 108. The reaction container 108 is, for example, a cuvette. The reaction container 108 has an agitator in advance. The first dispenser 150a moves the suction tube 153, and suctions a predetermined amount of specimen from the specimen container 104 disposed at the specimen suctioning position 501. The first dispenser 150b moves the suction tube 153 and suctions a predetermined amount of specimen from the specimen container 104 disposed at the specimen suctioning position 502. The first dispensers 150a, 150b that have suctioned the specimens move the suction tubes 153, and dispense the specimens into the reaction containers 108 disposed at predetermined specimen dispensing positions 503, 504.

The measurement sample preparation unit 12 includes a rotatable table 160 for transporting the reaction container 108. The rotatable table 160 is disposed outside the reagent preparation table 180. The rotatable table 160 is ring-shaped in a planar view, and is rotatable in the circumferential direction. The rotatable table 160 has a plurality of holding holes 161 arranged along the circumferential direction. The reaction containers 108 can be disposed one by one in the holding holes 161, respectively. The first dispensers 150a, 150b dispense the suctioned specimens into the reaction containers 108 held by the rotatable table 160. The first dispenser 150a, 150b can suction the specimen from the reaction container 108 which is disposed in the rotatable table 160 and stores the specimen.

The measurement sample preparation unit 12 includes a holding mechanism 170 that can transport the reaction container 108. The holding mechanism 170 can hold and move the reaction container 108. The holding mechanism 170 allows the reaction container 108 to be disposed in the holding hole 161 of the rotatable table 160. The holding mechanism 170 can take out the reaction container 108 from the holding hole 161 of the rotatable table 160, and can dispose the reaction container 108 at a reagent dispensing position 508 or on a heating table 190 described below. Furthermore, the holding mechanism 170 can transfer the held reaction container 108 to a disposal outlet 106.

The measurement sample preparation unit 12 includes the heating table 190 that can hold and heat the reaction container 108 into which the specimen has been dispensed. The heating table 190 has a plurality of holding holes 191 for holding a plurality of the reaction containers 108, respectively, which contain the specimens, and a holding mechanism 192 for holding and transferring the reaction container 108. In the heating table 190, a heater for heating the reaction containers 108 held in the plurality of holding holes 191, respectively, is incorporated.

The heating table 190 is a round table, and has the plurality of holding holes 191 arranged along the circumferential direction. The heating table 190 is rotatable in the circumferential direction, and can transfer the reaction containers 108 disposed in the plurality of holding holes 191, by its rotation, in the circumferential direction while the reaction containers 108 are heated by the heater at a predetermined temperature. The holding mechanism 192 can hold and transfer the reaction container 108 to dispose the reaction container 108 in the holding hole 191, or take out the reaction container 108 from the holding hole 191 to dispose the reaction container 108 at the reagent dispensing position 508.

The measurement sample preparation unit 12 further includes a holding mechanism 175 for transferring the reaction container 108. The holding mechanism 175 includes a moving mechanism for movement in X, Y, and Z directions that are the three orthogonal axial directions, and can hold and transfer the reaction container 108. The holding mechanism 175 can take out the reaction container 108 from the holding hole 191 of the heating table 190 and transfer the reaction container 108 to a reagent dispensing position 507.

Figure 5:
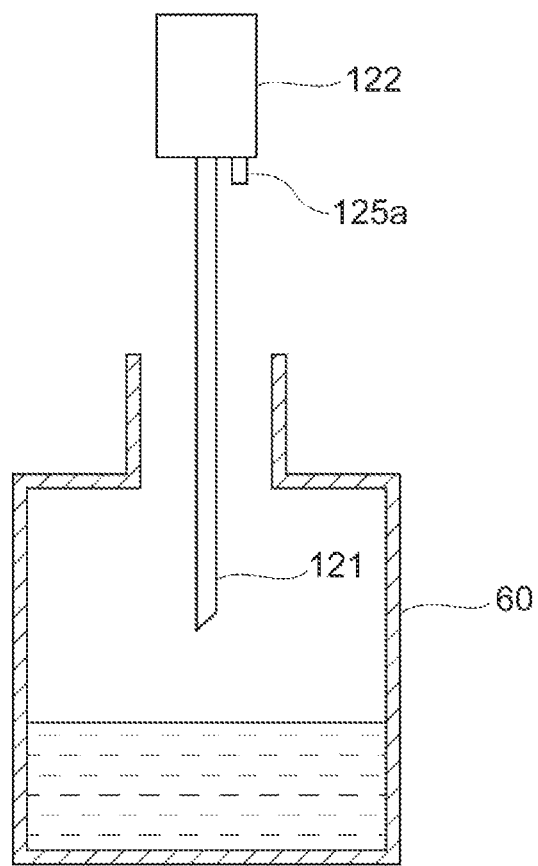
FIG. 5 is a schematic side view of a suction tube, a pump, and a solution amount detector of a second dispenser according to the embodiment.

The measurement sample preparation unit 12 includes second dispensers 120a, 120b. The second dispensers 120a, 120b each include a dispensing suction tube 121 as shown in FIG. 5. The suction tube 121 is connected to a pump 122, and can suction a predetermined amount of fluid and dispense the predetermined amount of the fluid. Each of the second dispensers 120a, 120b shown in FIG. 1 moves the suction tube 121 onto the diluted reagent solution container 60 disposed at a predetermined reagent suctioning position 505, 506 on the reagent preparation table 180 and suctions a predetermined amount of diluted reagent solution from the diluted reagent solution container 60. Thereafter, each of the second dispensers 120a, 120b moves onto the reaction container 108, and can dispense the predetermined amount of the diluted reagent solution into the reaction container 108 disposed at the reagent dispensing position 507, 508. Thus, the diluted reagent solution and the specimen are mixed in the reaction container 108, and a measurement sample containing a predetermined concentration of the reagent is prepared.

The number of the second dispensers is not particularly limited, and may be one or plural.

The measurement sample preparation unit 12 includes solution amount detectors 125a, 125b for detecting a storage amount of solution stored in each of the diluted reagent solution container 60 and the reaction container 108. The solution amount detectors 125a, 125b each include a liquid level detection sensor for detecting the height of the liquid level of the solution stored in each of the diluted reagent solution container 60 and the reaction container 108. The solution amount detector 125a shown in FIG. 5 includes a capacitance-type liquid level detection sensor. The liquid level detection sensor senses contact of the lower end of the suction tube 121 with the liquid level of the solution. As shown in FIG. 1, the solution amount detectors 125a, 125b are disposed at the second dispensers 120a, 120b.

Figure 6:
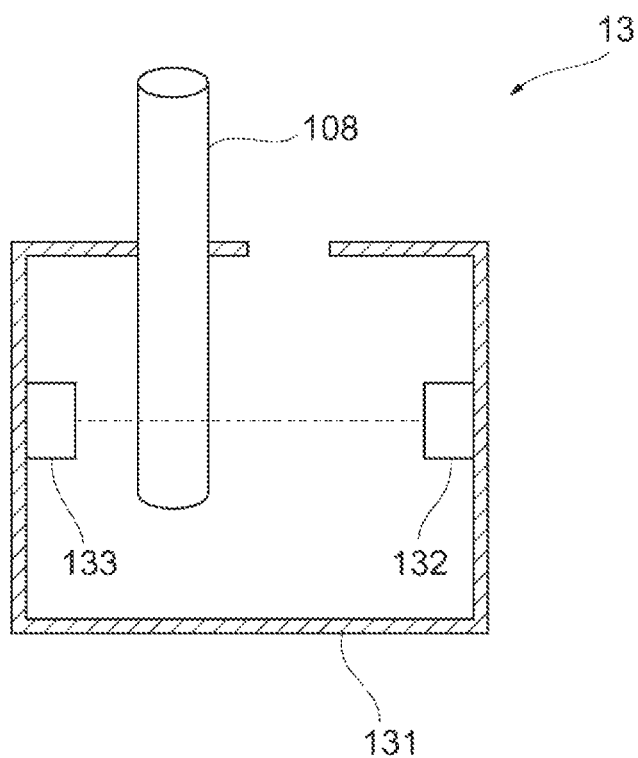
FIG. 6 is a schematic side view of a reaction container, a light transmitter, and a light receiver according to the embodiment.

The measurement unit 13 for performing optical measurement of a measurement sample measures an absorbance or a transmittance of the measurement sample. As shown in FIG. 6, the measurement unit 13 includes a container placement portion 131 at which the reaction container 108 containing a measurement sample is disposed, a light transmitter 132 for applying light for signal detection to the reaction container 108 disposed in the container placement portion 131, and a light receiver 133 disposed so as to correspond to the container placement portion 131. The container placement portion 131 may include an agitating mechanism for rotating the agitator in the reaction container 108.

For example, the measurement unit 13 includes a plurality of the container placement portions 131 shown in FIG. 1. The plurality of the container placement portions 131 may be linearly arranged in two lines so as to be spaced from each other over a predetermined distance. Thus, measurement samples in a plurality of the reaction containers 108 can be measured.

The holding mechanism 175 transfers the reaction container 108 that stores the measurement sample, from the reagent dispensing position 507, to the container placement portion 131 of the measurement unit 13.

The measurement unit 13 measures temporal change of an absorbance or a transmittance during agglutination reaction of, for example, platelets in the measurement sample in the reaction container 108 disposed in the container placement portion 131. The light transmitter 132 applies light to the measurement sample which is being agitated in the reaction container 108 disposed in the container placement portion 131. The light transmitter 132 includes a light source such as a light emitting diode and a halogen lamp. The light transmitter 132 may include a light guide such as an optical fiber for transmitting light from the light source into the container placement portion 131. The light receiver 133 receives transmitted light or scattered light of the light applied to the measurement sample in the reaction container 108, and outputs an electric signal corresponding to an amount of received light. The light receiver 133 includes a photoelectric conversion element for converting the received light to an electric signal and outputting the electric signal. The electric signal is transmitted to the analyzer 140 described below. The holding mechanism 175 can take out the reaction container 108 having been measured, from the container placement portion 131, and transfer the reaction container 108 to the disposal outlet 106.

The analyzer 140 is connected to the specimen measurement apparatus 200, and analyzes platelet aggregation of a specimen based on the electric signal outputted by the light receiver 133 of the specimen measurement apparatus 200. The analyzer 140 calculates vWF:RCo (von Willebrand factor ristocetin cofactor) activity, the adenosine diphosphate (ADP) maximum aggregation rate, the collagen maximum aggregation rate, the epinephrine maximum aggregation rate, the arachidonic acid maximum aggregation rate, the ristocetin maximum aggregation rate, the protease-activated receptor 1-activating peptide (PAR1-AP) maximum aggregation rate, and the like, based on an absorbance or a transmittance of the measurement sample.

Figure 7:
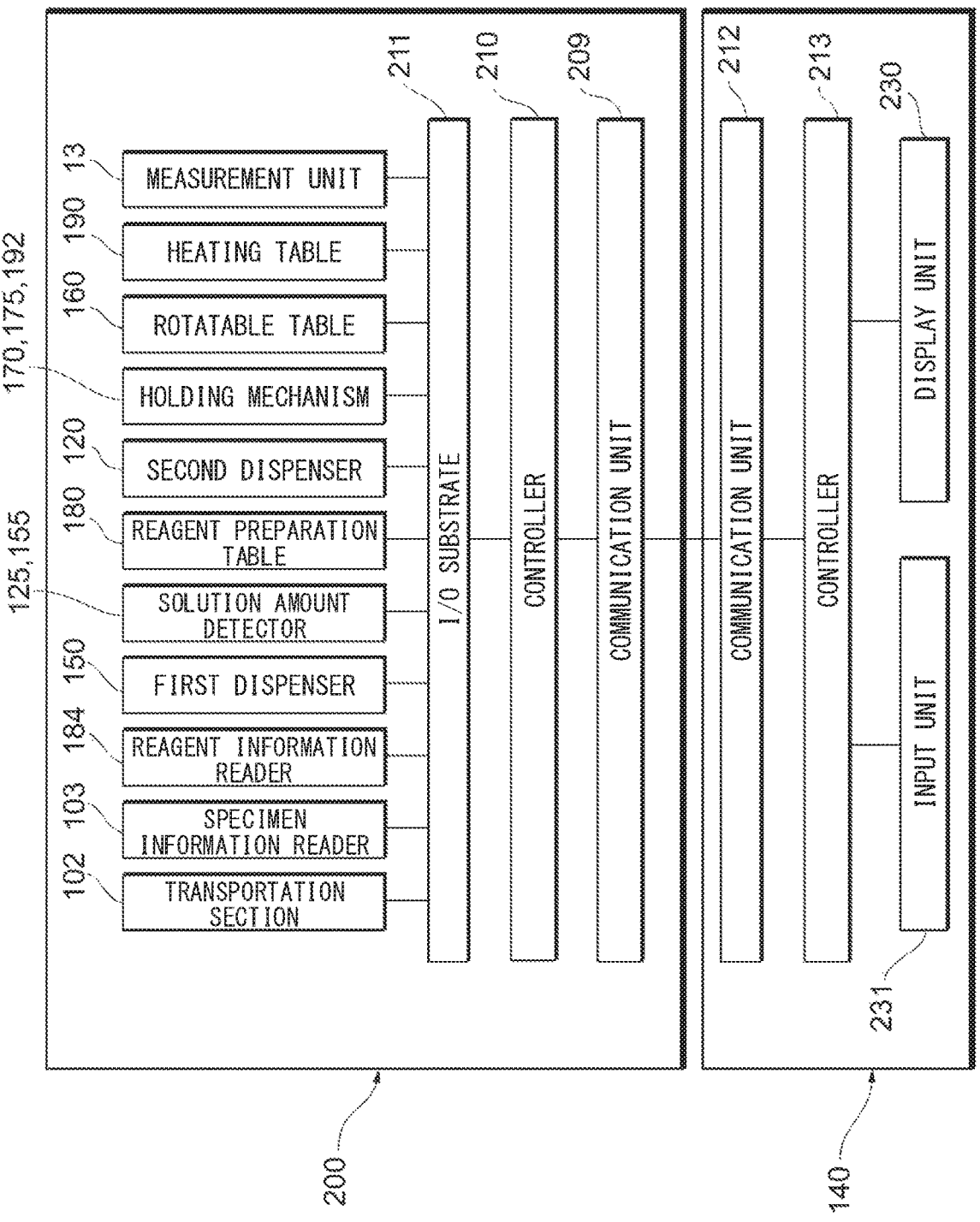
FIG. 7 is a block diagram illustrating the specimen measurement apparatus according to the embodiment.

FIG. 7 is a block diagram illustrating relationship between components of the specimen measurement apparatus 200 and the analyzer 140 shown in FIG. 1, and controllers 210, 213 for controlling the components according to control signals. The controller 210 includes a processor such as a CPU (central processing unit) or a FPGA (field-programmable gate array), and a volatile and/or a non-volatile storage device such as a ROM (read only memory), a RAM (random access memory), and a hard disk.

The processor of the controller 210 executes a control program stored in the storage device, to control the components of the specimen measurement apparatus 200 via an I/O substrate 211. Specifically, the controller 210 controls, for example, a dispensing operation of the second dispenser 120, dispensing operations of the first dispensers 150a, 150b, an operation of the reagent preparation table 180, operations of each rotatable table and each holding mechanism, light transmission and reception of the light transmitter 132 and the light receiver 133 of the measurement unit 13.

The specimen measurement apparatus 200 includes a communication unit 209, and the analyzer 140 includes a communication unit 212. The specimen measurement apparatus 200 and the analyzer 140 perform transmission and reception of information therebetween via the communication units 209, 212.

The analyzer 140 has a controller 213 that includes a processor such as a CPU, and a storage device such as a ROM, a RAM, and a hard disk. The controller 213 of the analyzer 140 analyzes platelet aggregation of a specimen based on an electric signal outputted from the light receiver 133 of the specimen measurement apparatus 200. To the analyzer 140, a display unit 230 capable of displaying a screen, and an input unit 231 capable of performing input to the controllers 210, 213 are connected.

In the example shown in FIG. 7, the two controllers 210, 213 are disposed. However, the number of the controllers is not particularly limited. One controller may control the specimen measurement apparatus 200 and the analyzer 140, or three or more controllers may control the specimen measurement apparatus 200 and the analyzer 140. The arrangement of the controllers is not particularly limited, and the controllers may be disposed in one of the specimen measurement apparatus 200 or the analyzer 140, or the controller may be disposed outside the specimen measurement apparatus 200 and the analyzer 140.

Next, a specimen measurement method for measuring platelet aggregation of a specimen according to the embodiment will be described.

Figure 8:
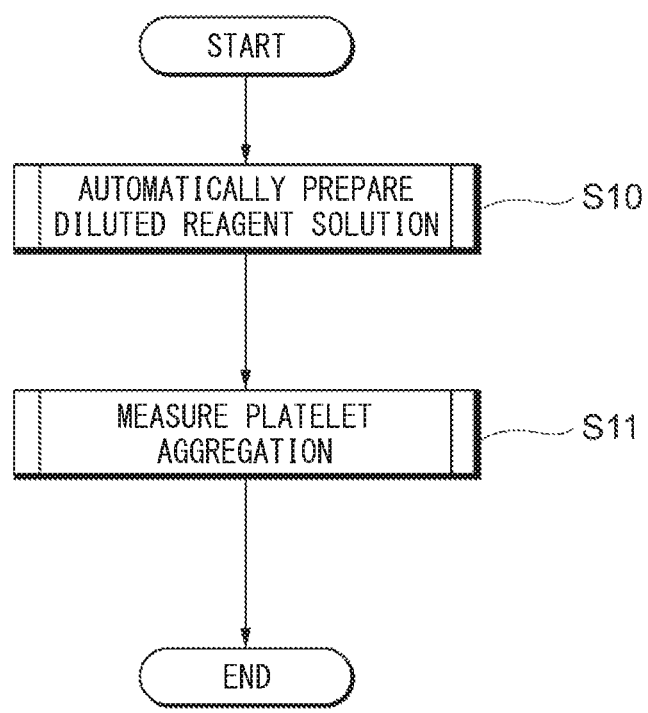
FIG. 8 is a flow chart showing a specimen measurement method according to the embodiment.

As shown in FIG. 8, the specimen measurement method according to the embodiment includes step S10 of automatically preparing a diluted reagent solution that contains a platelet-aggregating reagent diluted with a diluent, and step S11 of preparing a measurement sample that contains a predetermined concentration of the platelet-aggregating reagent, from the diluted reagent solution and a specimen, and performing optical measurement of the measurement sample.

Figure 9:
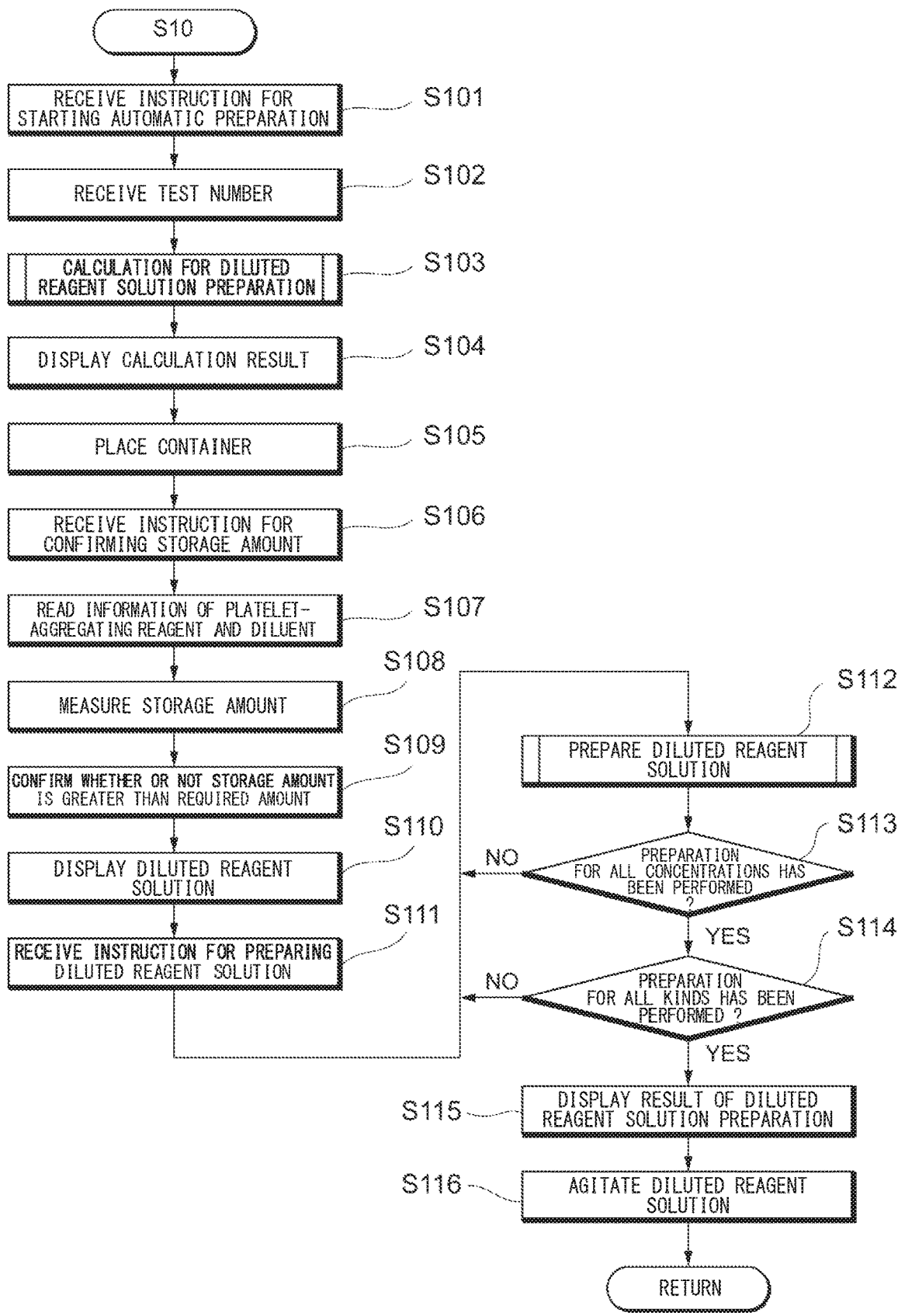
FIG. 9 is a flow chart showing the specimen measurement method according to the embodiment.
Figure 10:
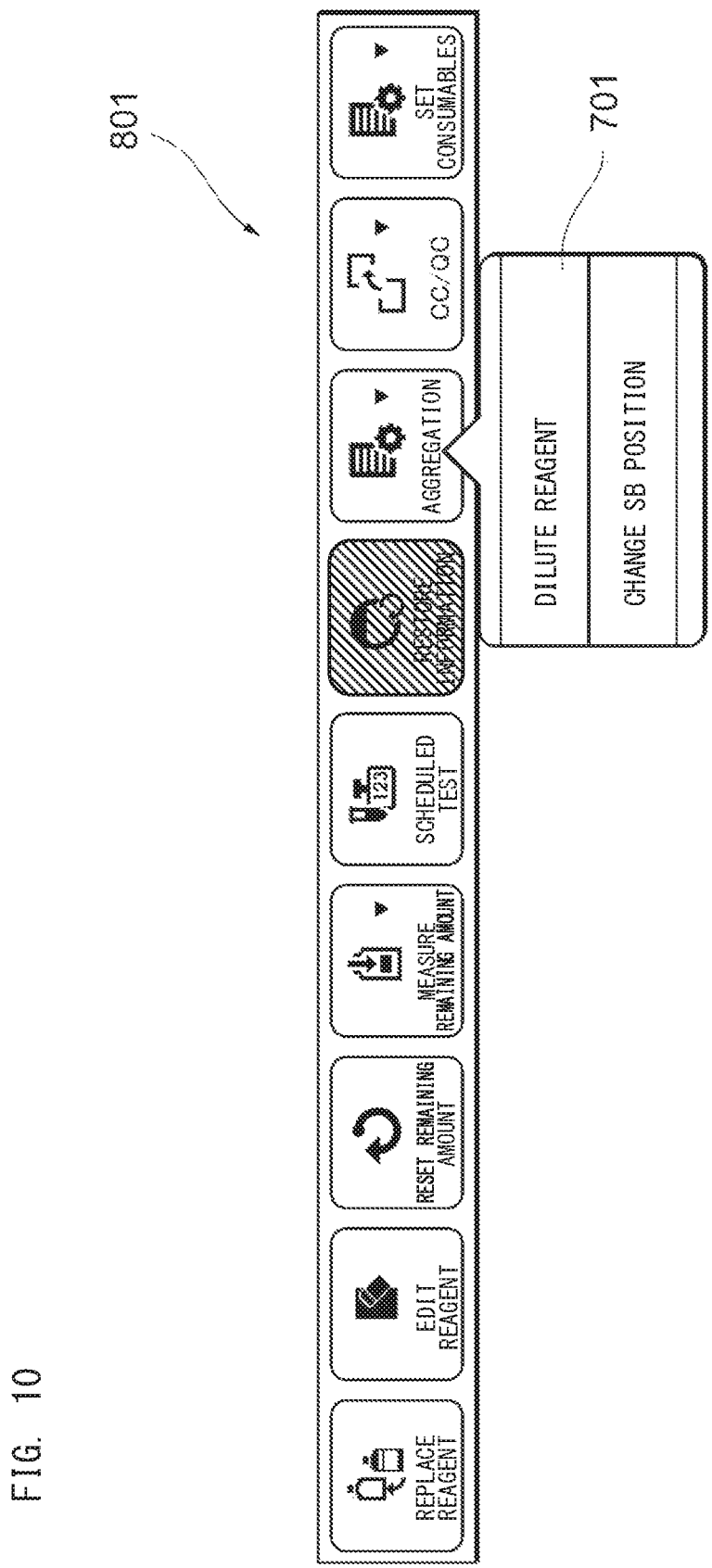
FIG. 10 is a schematic diagram illustrating a screen representing a menu for starting an automatic preparation step of automatically preparing a diluted reagent solution, according to the embodiment.

FIG. 9 shows step S10 in detail. In step S101, the controller 210 controls the display unit 230 such that the display unit 230 displays a menu 801 for starting an automatic preparation step of automatically preparing a diluted reagent solution as shown in FIG. 10. When a user clicks a reagent dilution button 701 through the input unit 231, the controller 210 receives an instruction for starting the automatic preparation step of automatically preparing the diluted reagent solution. As shown in FIG. 11, the controller 210 controls the display unit 230 such that the display unit 230 displays a test number input screen 802 that includes combinations 702 each including a preset kind of platelet-aggregating reagent, and a preset predetermined concentration of the platelet-aggregating reagent in the measurement sample. In the example shown in FIG. 11, the predetermined concentration of the platelet-aggregating reagent in the measurement sample is displayed as a final concentration.

In step S102, when the user inputs the test number corresponding to a combination of the kind of the platelet-aggregating reagent and the predetermined concentration of the platelet-aggregating reagent in the measurement sample, into an input box 703, through the input unit 231, the controller 210 receives the test number corresponding to the combination of the kind of the platelet-aggregating reagent and the predetermined concentration of the platelet-aggregating reagent in the measurement sample. The test number represents the number of times the measurement sample is prepared and measured under the same condition in step S11. Among the combinations each including the kind of the platelet-aggregating reagent and the predetermined concentration of the platelet-aggregating reagent in the measurement sample, a combination for which the test number is set is a combination selected for automatically preparing the diluted reagent solution, and a combination for which the test number is not set is a combination which is not selected for automatically preparing a diluted reagent solution. The controller 210 causes the storage device to store the inputted test number. When the controller 210 receives click of a presetting storage button 704 from the user through the input unit 231, the controller 210 causes the storage device to store the inputted test number as the preset test number. When the controller 210 receives click of a presetting reading button 705 from the user through the input unit 231, the controller 210 causes the storage device to read the preset test number, and controls the display unit 230 such that the display unit 230 displays the preset test number.

In step S103, when the user clicks a required amount calculation button 706 through the input unit 231, and the controller 210 receives an instruction from the user for starting calculation necessary for automatically preparing the diluted reagent solution, the specimen measurement apparatus 200 performs calculation necessary for automatically preparing the diluted reagent solution.

Figure 12:
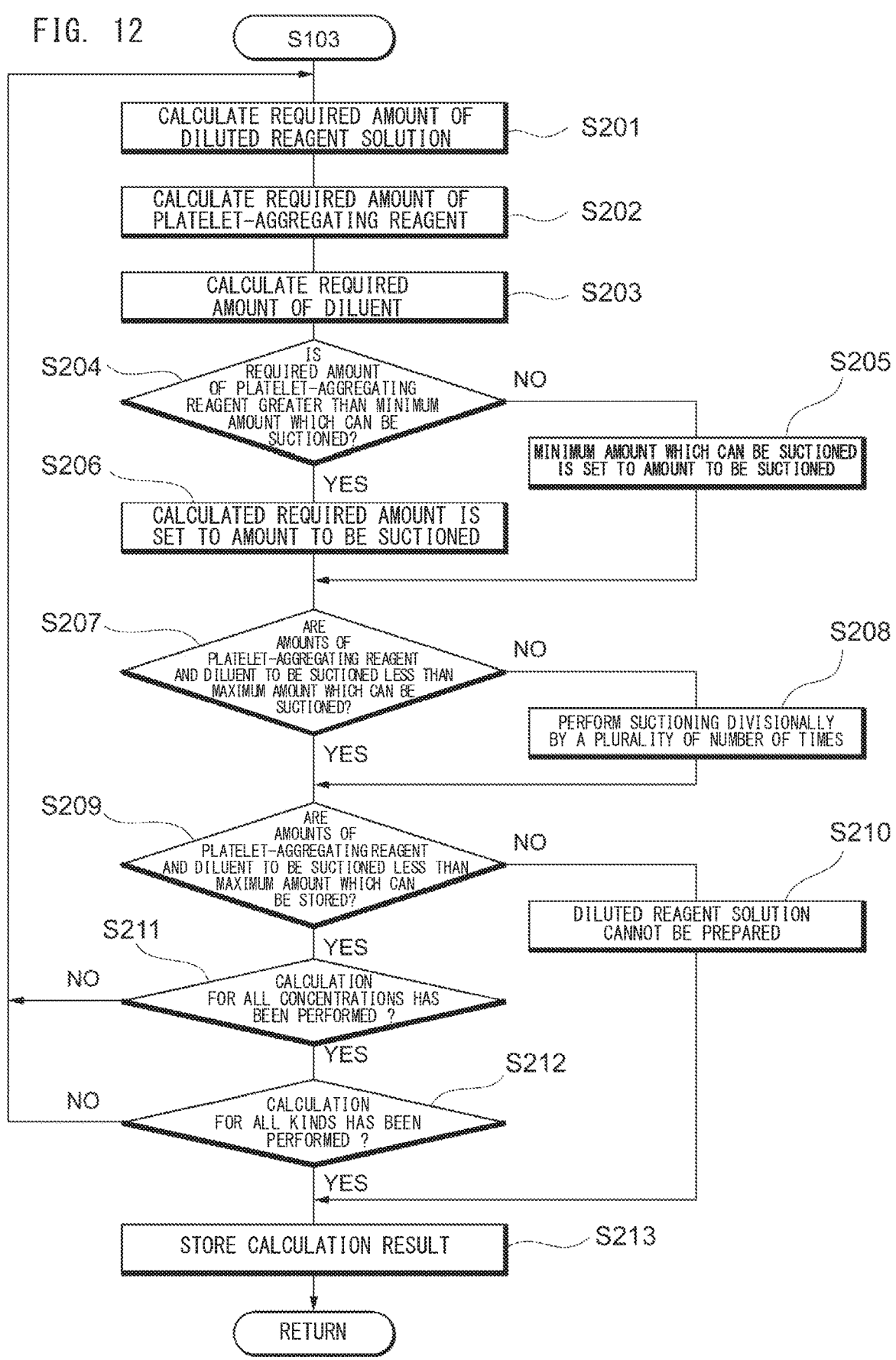
FIG. 12 is a flow chart showing the specimen measurement method according to the embodiment.

Specifically, in step S201 shown in FIG. 12, the controller 210 calculates a required amount $V_T$ of a diluted reagent solution for one combination of the kind of the platelet-aggregating reagent and the predetermined concentration of the platelet-aggregating reagent in the measurement sample by using the flowing equation (1).

$$V_T = V_1 \times T + V_D \qquad (1)$$

where $V_1$ represents a predetermined amount, of the diluted reagent solution, required for one test, T represents a set test number, and $V_D$ represents a dead volume in the diluted reagent solution container 60. The predetermined amount $V_1$, of the diluted reagent solution, required for one test and the dead volume $V_D$ in the diluted reagent solution container 60 are constants that depend on, for example, the characteristics and the size of the specimen measurement apparatus 200. The amount $V_1$, of the diluted reagent solution, required for one test is, for example, 20 μL. The dead volume $V_D$ in the diluted reagent solution container 60 is, for example, 30 μL. The test number T is any value set in step S102.

In step S202, the controller 210 calculates a required amount $V_0$ of a platelet-aggregating reagent corresponding to one combination of the kind of the platelet-aggregating reagent and the predetermined concentration of the platelet-aggregating reagent in the measurement sample, by using the following equation (2).

$$V_0 = C_F \div C_0 \times V_T \times D \quad (2)$$

where $C_F$ represents the predetermined concentration of the platelet-aggregating reagent in the measurement sample, $C_0$ represents a concentration of the platelet-aggregating reagent in a solution containing the platelet-aggregating reagent in the reagent container 90, and D represents a dilution rate of the diluted reagent solution at the time of preparation of the measurement sample. The dilution rate D is obtained by dividing the sum of an amount of the diluted reagent solution and an amount of the specimen by the amount of the diluted reagent solution when the measurement sample is prepared. The predetermined concentration $C_F$ of the platelet-aggregating reagent in the measurement sample is any set value. The concentration $C_0$ of the platelet-aggregating reagent in the solution containing the platelet-aggregating reagent in the reagent container 90 is a constant. For example, when the platelet-aggregating reagent is ADP, the concentration $C_0$ of the platelet-aggregating reagent in the solution containing the platelet-aggregating reagent is 160 μmol/L. The dilution rate D depends on, for example, the characteristics and the size of the specimen measurement apparatus 200. For example, when the predetermined amount $V_1$ of the diluted reagent solution required for one test is 20 μL and a predetermined amount $V_S$ of the specimen is 140 μL, the dilution rate D is eight times.

In step S203, the controller 210 calculates a required amount $V_B$ of the diluent corresponding to one combination of the kind of the platelet-aggregating reagent and the predetermined concentration of the platelet-aggregating reagent in the measurement sample by using the following equation (3).

$$V_B = V_T - V_0 \quad (3)$$

In step S204, the controller 210 determines whether or not the required amount $V_0$ of the platelet-aggregating reagent calculated in step S202 is greater than a minimum value $V_m$ of an amount of the platelet-aggregating reagent which can be suctioned by the first dispenser 150a. The minimum value $V_m$ is, for example, 4 μL. When the required amount $V_0$ is less than the minimum value $V_m$, the controller 210 substitutes the minimum value $V_m$ of the amount of the platelet-aggregating reagent which can be suctioned by the first dispenser 150a, for the required amount $V_0$ of the platelet-aggregating reagent, in step S205. Furthermore, the controller 210 calculates a corrected required amount $V_{BC}$ of the diluent by using the following equation (4).

$$V_{BC} = V_m / V_0 \times V_B \quad (4)$$

The controller 210 determines that the first dispenser 150a suctions the platelet-aggregating reagent by the minimum value $V_m$ of an amount of the platelet-aggregating reagent that can be suctioned, and the first dispenser 150a suctions the corrected required amount $V_{BC}$ of the diluent, to produce the diluted reagent solution corresponding to one combination of the kind of the platelet-aggregating reagent and the predetermined concentration of the platelet-aggregating reagent in the measurement sample. The first dispenser 150b may be used. The same applies to the following description.

When the required amount $V_0$ of the platelet-aggregating reagent calculated in step S202 is greater than the minimum value $V_m$ of the amount of the platelet-aggregating reagent which can be suctioned by the first dispenser 150a, the controller 210 determines in step S206 that the first dispenser 150a suctions the required amount $V_0$ of the platelet-aggregating reagent calculated in step S202, and the first dispenser 150a suctions the required amount $V_B$ of the diluent calculated in step S203, to produce the diluted reagent solution corresponding to one combination of the kind of the platelet-aggregating reagent and the predetermined concentration of the platelet-aggregating reagent in the measurement sample.

When step S205 is performed, the controller 210 determines in step S207 whether or not the total amount, of the platelet-aggregating reagent and the diluent, which is the sum of the corrected required amount $V_{BC}$ and the minimum value $V_m$ of the amount of the platelet-aggregating reagent which can be suctioned is less than a maximum value $V_M$ of the amount which can be suctioned by the first dispenser 150a. When step S206 is performed, the controller 210 determines in step S207 whether or not the total amount, of the platelet-aggregating reagent and the diluent, which is the sum of the required amount $V_0$ and the required amount $V_B$ is less than the maximum value $V_M$ of the amount which can be suctioned by the first dispenser 150a. The maximum value $V_M$ is, for example, 250 μL.

When the total amount of the platelet-aggregating reagent and the diluent is greater than the maximum value $V_M$, the controller 210 calculates a natural number in step S208 such that a value obtained by dividing the total amount of the platelet-aggregating reagent and the diluent by the natural number is greater than the minimum value $V_m$ and less than the maximum value $V_M$. The controller 210 determines that the platelet-aggregating reagent and the diluent are to be suctioned divisionally by the number of times corresponding to the calculated natural number.

In step S209, the controller 210 determines whether or not the total amount of the platelet-aggregating reagent and the diluent which are suctioned by the first dispenser 150a is less than a maximum value $V_R$ of an amount which can be stored in the diluted reagent solution container 60. The maximum value $V_R$ is, for example, 3000 μL. When the total amount is greater than the maximum value $V_R$ for the diluted reagent solution container 60, the controller 210 controls the display unit 230 in step S210 such that the display unit 230 indicates that the diluted reagent solution cannot be prepared in the set combination of the kind of the platelet-aggregating reagent and the predetermined concentration of the platelet-aggregating reagent in the measurement sample.

In step S211, the controller 210 determines whether or not the required amount of the platelet-aggregating reagent and the required amount of the diluent for all of the plurality of predetermined concentrations of the platelet-aggregating reagent in the measurement sample have been calculated. When the required amount of the platelet-aggregating reagent and the required amount of the diluent for all the plurality of predetermined concentrations of the platelet-aggregating reagent in the measurement sample have not been calculated, the process is returned to step S201. When the required amount of the platelet-aggregating reagent and the required amount of the diluent for all of the plurality of predetermined concentrations of the platelet-aggregating reagent in the measurement sample have been calculated, the process proceeds to step S212.

In step S212, the controller 210 determines whether or not the required amount of the platelet-aggregating reagent and the required amount of the diluent for all of the plurality of kinds of the platelet-aggregating reagents have been calculated. When the required amount of the platelet-aggregating reagent and the required amount of the diluent for all of the plurality of kinds of the platelet-aggregating reagents have not been calculated, the process is returned to step S201. When the required amount of the platelet-aggregating reagent and the required amount of the diluent for all of the plurality of kinds of the platelet-aggregating reagents have been calculated, the process proceeds to step S213.

In step S213, the controller 210 causes the storage device to store the required amount of the platelet-aggregating reagent and the required amount of the diluent which are determined for each combination of the kind of the platelet-aggregating reagent and the predetermined concentration of the platelet-aggregating reagent in the measurement sample.

Figure 14:
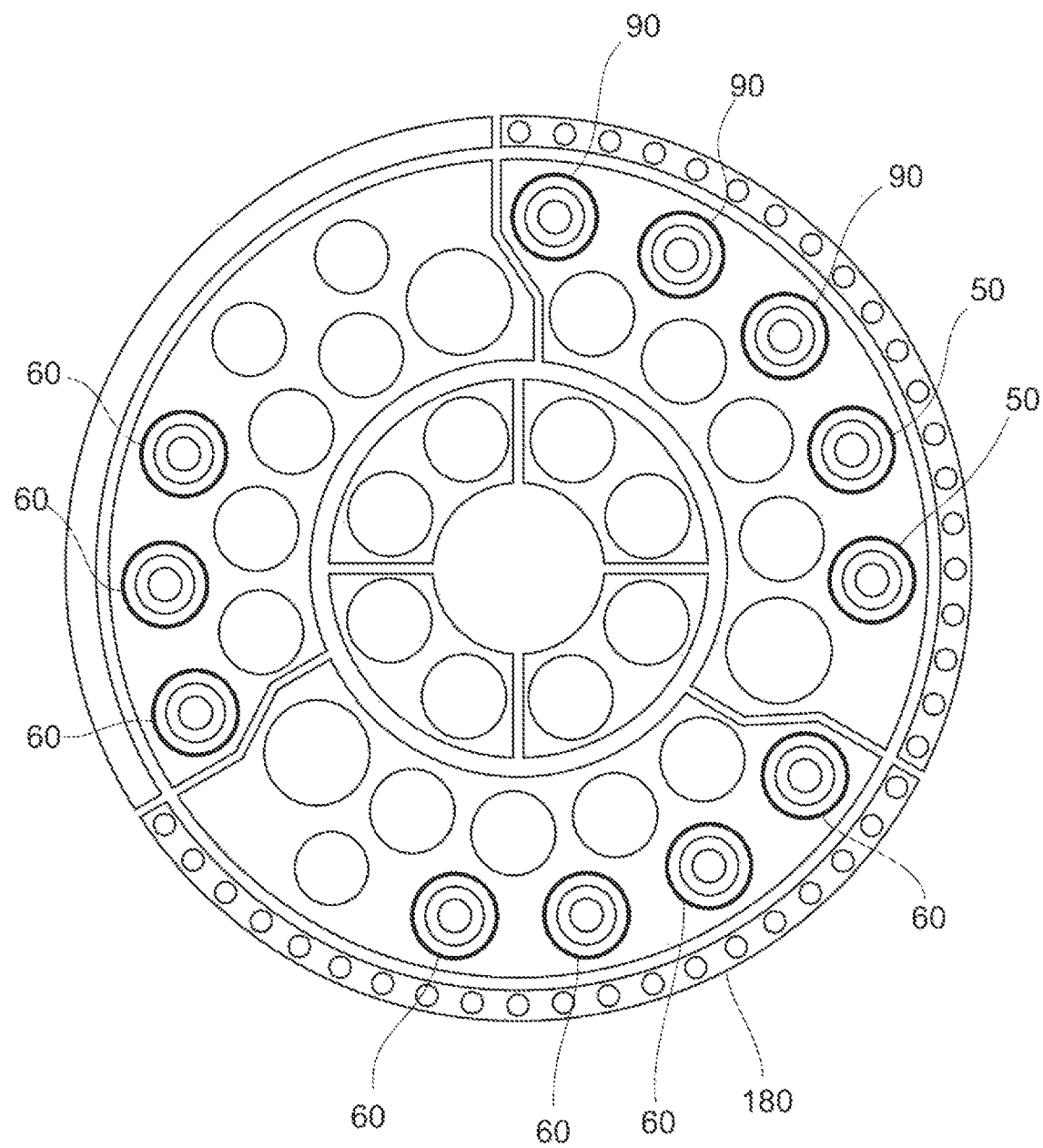
FIG. 14 is a schematic top view of a reagent preparation table according to the embodiment.

In step S104 in FIG. 9, the controller 210 controls the display unit 230 such that the display unit 230 displays a reagent preparation screen 803 indicating a required reagent amount 707 and a required diluent amount 708 as shown in FIG. 13. In step S105, as shown in FIG. 14, the user places the reagent container 90, the diluent container 50, and the diluted reagent solution container 60 in the reagent preparation table 180. In step S106, when the user clicks a remaining amount measurement button 709 shown in FIG. 13 through the input unit 231, the controller 210 receives an instruction for starting measuring a storage amount (remaining amount) of the platelet-aggregating reagent in the reagent container 90 and a storage amount (remaining amount) of the diluent in the diluent container 50.

In step S107, the controller 210 controls the display unit 230 such that the display unit 230 displays a dialog box 710 for confirming that reagent information is read and the storage amount (remaining amount) of the platelet-aggregating reagent and the storage amount (remaining amount) of the diluent are measured as shown in FIG. 15. When the controller 210 receives an instruction for starting reading reagent information and measuring the storage amount (remaining amount) of the platelet-aggregating reagent and the storage amount (remaining amount) of the diluent, from the user, through the input unit 231, the controller 210 causes the reagent preparation table 180 to rotate and move each of the reagent container 90, the diluent container 50, and the diluted reagent solution container 60 to a position in front of the reagent information reader 184. The controller 210 causes the reagent information reader 184 to read the identification information of each of the reagent container 90, the diluent container 50, and the diluted reagent solution container 60, and causes the reagent information reader 184 to specify positioning of the reagent container 90, the diluent container 50, and the diluted reagent solution container 60. The controller 210 controls the reagent information reader 184 to store, in the storage device, the identification information and positioning of the reagent container 90, the diluent container 50, and the diluted reagent solution container 60. The identification information read by the reagent information reader 184 may merely contain the identification number (ID), and the controller 210 may receive information such as a name of the content, a kind of the content, a concentration of the content in a solution containing the content, a lot number, and an expiration date, which correspond to the identification number (ID), via a network from a server, and cause the storage device to store the information.

In step S108, the controller 210 controls the solution amount detector 155a to measure a storage amount of a solution stored in each of the reagent container 90 and the diluent container 50 disposed in the reagent preparation table 180, and causes the storage device to store the measured amounts of the solutions. The controller 210 causes the display unit 230 to display a reagent preparation screen 804 indicating the measured storage amount, as shown in FIG. 16. In the example shown in FIG. 16, the storage amount is displayed in a current amount column 711.

When the user clicks a to-the-next button 712 through the input unit 231, the controller 210 determines in step S109 whether or not the sum of the required amounts of the platelet-aggregating reagent determined for each combination of the kind of the platelet-aggregating reagent and the predetermined concentration of the platelet-aggregating reagent in the measurement sample is less than the storage amount of the solution, containing the platelet-aggregating reagent, which is stored in the reagent container 90. The controller 210 also determines whether or not the sum of the required amounts of the diluent determined for each combination of the kind of the platelet-aggregating reagent and the predetermined concentration of the platelet-aggregating reagent in the measurement sample is less than the storage amount of the diluent stored in the diluent container 50.

In step S110, the controller 210 controls the display unit 230 such that the display unit 230 displays a dilution execution confirmation screen 805 including a list 713 of the diluted reagent solutions to be produced, as shown in FIG. 17. When some of the diluted reagent solutions cannot be produced since the sum of the required amounts of the platelet-aggregating reagent or the diluent is greater than the storage amount, an error is indicated in an error column 714. For example, when the storage amount of the platelet-aggregating reagent or the diluent is short, the diluted reagent solution having a lower concentration is preferentially produced.

In step S111, when the user clicks an execution button 715 through the input unit 231, the controller 210 receives an instruction for starting automatically preparing the diluted reagent solution.

Figure 18:
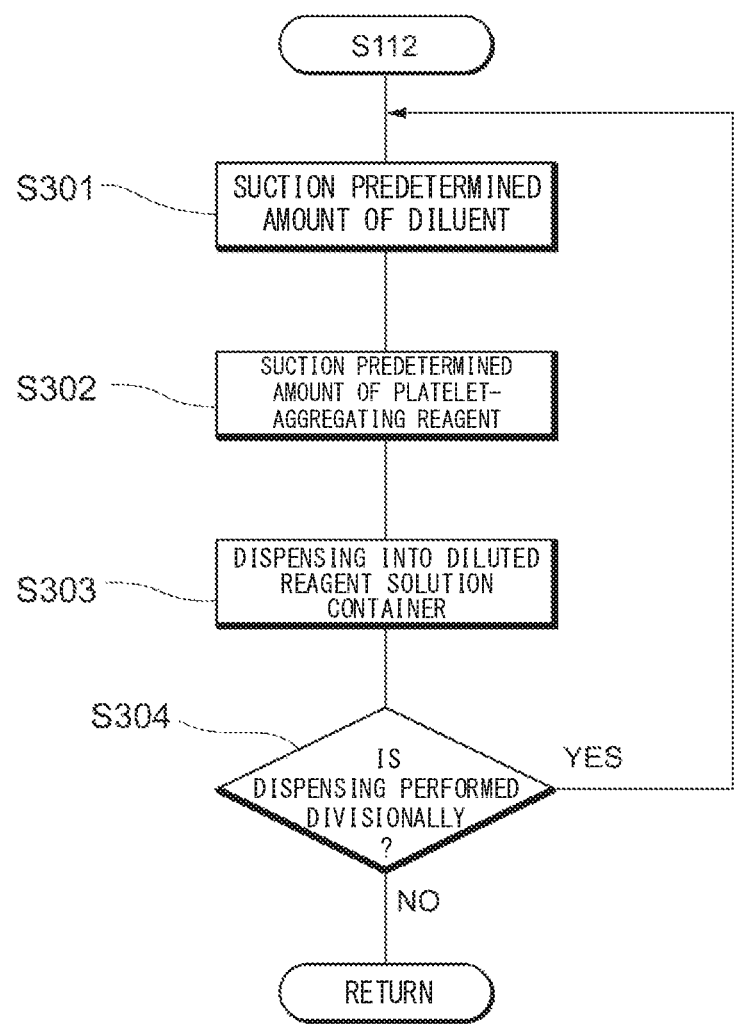
FIG. 18 is a flow chart showing the specimen measurement method according to the embodiment.

In step S112, the controller 210 causes the diluted reagent solution preparation unit 11 to prepare the diluted reagent solution by using the required amount of the platelet-aggregating reagent and the required amount of diluent determined for each combination of the kind of the platelet-aggregating reagent and the predetermined concentration of the platelet-aggregating reagent in the measurement sample. Specifically, in step S301 in FIG. 18, the controller 210 causes the first dispenser 150a to move onto the diluent container 50, and suction the diluent from the diluent container 50 according to the required amount of the diluent determined for each combination of the kind of the platelet-aggregating reagent and the predetermined concentration of the platelet-aggregating reagent in the measurement sample. Subsequently, in step S302, the controller 210 causes the first dispenser 150a to move onto the reagent container 90 while holding the diluent, and suction the platelet-aggregating reagent from the reagent container 90 according to the required amount of the platelet-aggregating reagent determined for each combination of the kind of the platelet-aggregating reagent and the predetermined concentration of the platelet-aggregating reagent in the measurement sample. In step S303, the controller 210 causes the first dispenser 150a to move onto the diluted reagent solution container 60, and dispense the held diluent and platelet-aggregating reagent into the diluted reagent solution container 60, thereby preparing the diluted reagent solution corresponding to the set combination of the kind of the platelet-aggregating reagent and the predetermined concentration of the platelet-aggregating reagent in the measurement sample. When the diluent and the platelet-aggregating reagent are determined in step S208 to be suctioned divisionally by a plurality of number of times, the process is returned from step S304 to step S301.

In step S113 in FIG. 9, the controller 210 determines whether or not all the diluted reagent solutions have been prepared for the plurality of predetermined concentrations of the platelet-aggregating reagent in the measurement sample. When all the diluted reagent solutions have not been prepared for the plurality of predetermined concentrations of the platelet-aggregating reagent in the measurement sample, the process is returned to step S112. When all the diluted reagent solutions have been prepared for the plurality of predetermined concentrations of the platelet-aggregating reagent in the measurement sample, the process proceeds to step S114.

Figure 19:
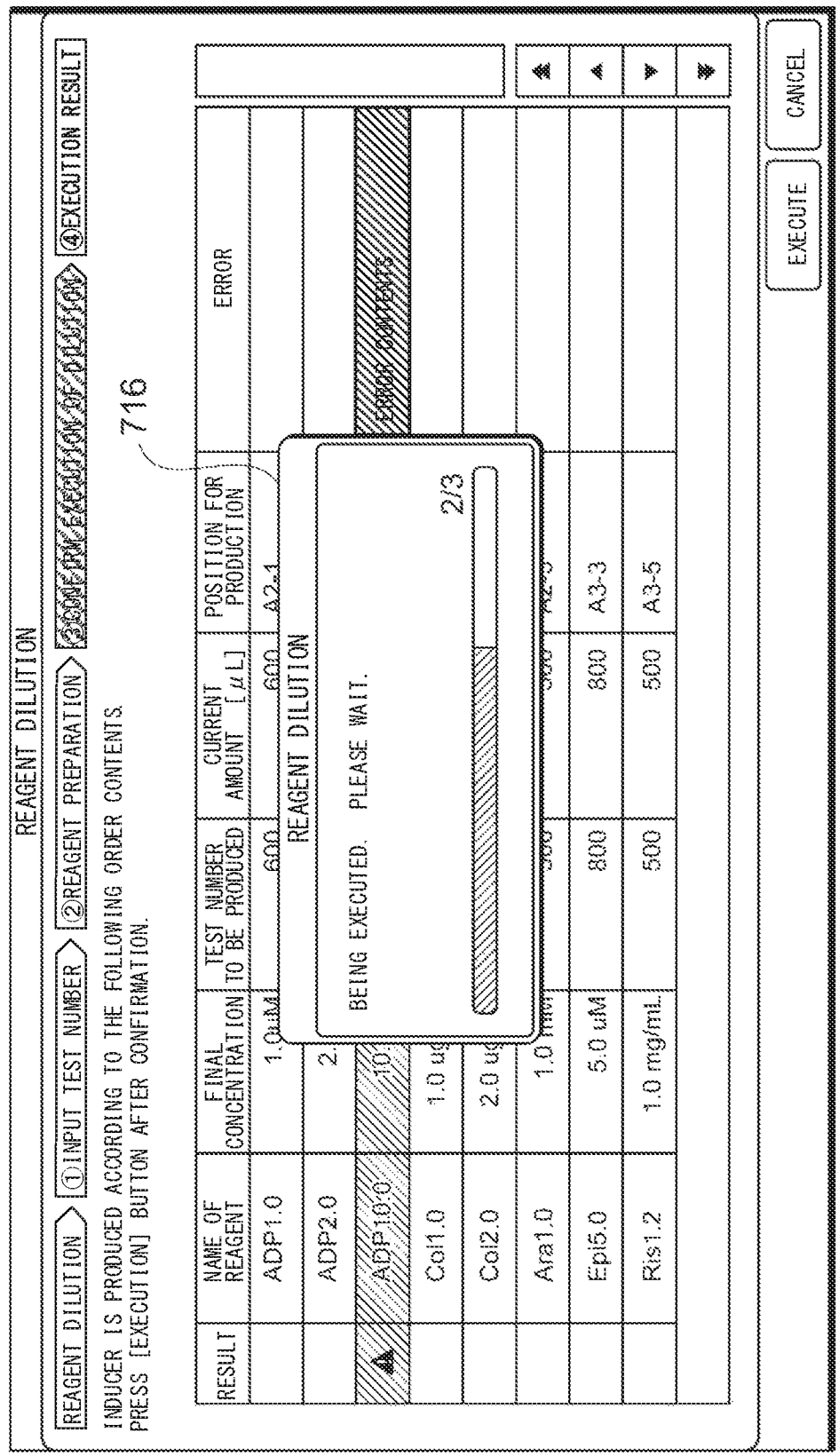
FIG. 19 is a schematic diagram illustrating the dilution execution confirmation screen and a dialog box according to the embodiment.

In step S114, the controller 210 determines whether or not all the diluted reagent solutions have been prepared for the plurality of kinds of the platelet-aggregating reagents. When all the diluted reagent solutions have not been prepared for the plurality of kinds of the platelet-aggregating reagents, the process is returned to step S112. While the diluted reagent solutions are prepared, the controller 210 controls the display unit 230 such that the display unit 230 displays a dialog 716 indicating that the diluted reagent solutions are being prepared, as shown in FIG. 19. When all the diluted reagent solutions have been prepared for the plurality of kinds of the platelet-aggregating reagents, the process proceeds to step S115.

In step S115, the controller 210 causes the display unit 230 to display an execution result display screen 806 that includes a list 717 of the prepared diluted reagent solutions, as shown in FIG. 20. When some of the diluted reagent solutions cannot be produced since the sum of the required amounts of the platelet-aggregating reagent or the diluent is greater than the storage amount, an error is displayed in an error column 718. In step S116, the controller 210 may cause the display unit 230 to display a message for promoting agitation of the prepared diluted reagent solution.

In step S11 in FIG. 8, platelet aggregation of the specimen is measured. Specifically, in step S401 in FIG. 21, the specimen container 104 containing the PPP specimen and the specimen container 104 containing the PRP specimen are disposed in the transportation section 102. The controller 210 causes the specimen information reader 103 to read the identification information adhered to the specimen container 104, and causes the storage device to store the information. In step S402, the controller 210 causes the measurement sample preparation unit 12 to prepare the measurement sample corresponding to each of the combinations each including the kind of the platelet-aggregating reagent and the predetermined concentration of the platelet-aggregating reagent in the measurement sample.

Figure 22:
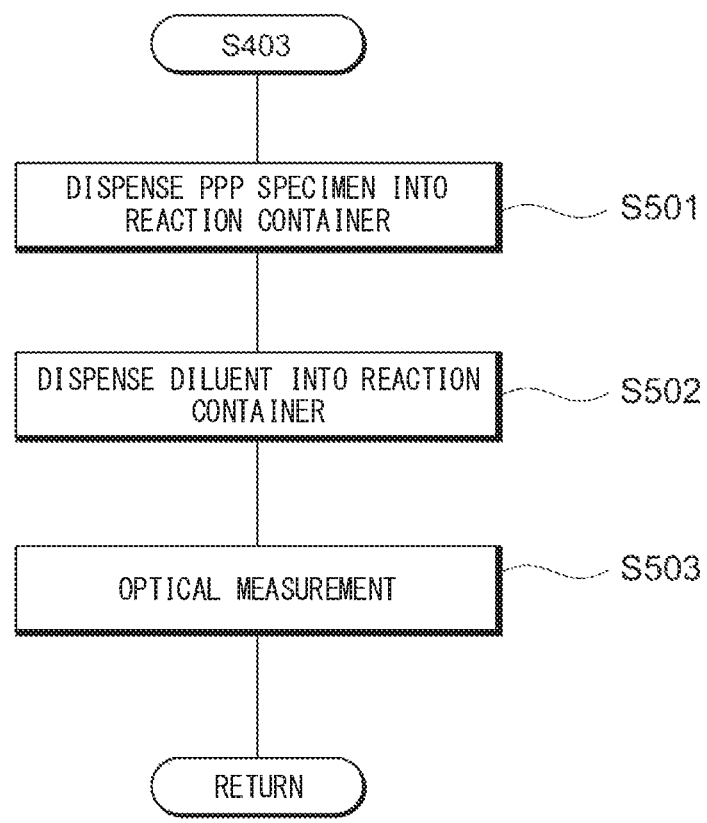
FIG. 22 is a flow chart showing the specimen measurement method according to the embodiment.

In step S403, the controller 210 causes the measurement sample preparation unit 12 to prepare a measurement sample of the PPP specimen, and causes the measurement unit 13 to measure the measurement sample of the PPP specimen. Specifically, in step S501 in FIG. 22, the controller 210 causes the first dispenser 150a to suction a predetermined amount of the PPP specimen from the specimen container 104 that has been determined to contain the PPP specimen, and dispense the PPP specimen into the reaction container 108. In step S502, the controller 210 causes the second dispenser 120a to suction a predetermined amount of diluent from the diluent container 50 and dispense the diluent into the reaction container 108 to dilute the PPP specimen. In step S503, the controller 210 causes the holding mechanism 175 to transfer, to the measurement unit 13, the reaction container 108 that stores the diluted PPP specimen, and causes the measurement unit 13 to measure temporal change of an absorbance or a transmittance of the diluted PPP specimen in the reaction container 108, for a predetermined period of time. The controller 210 causes the storage device to store the temporal change, of the absorbance or the transmittance of the PPP specimen, which is measured by the measurement unit 13.

Figure 21:
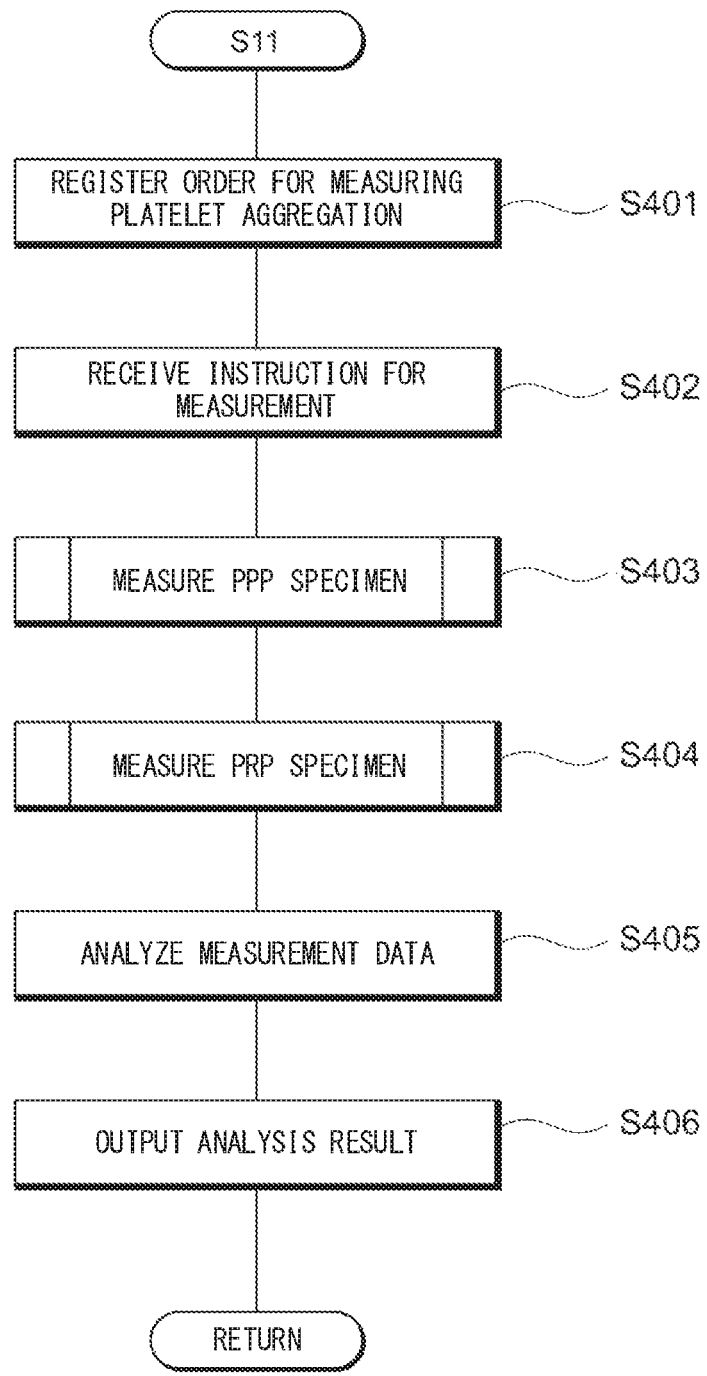
FIG. 21 is a flow chart showing the specimen measurement method according to the embodiment.
Figure 23:
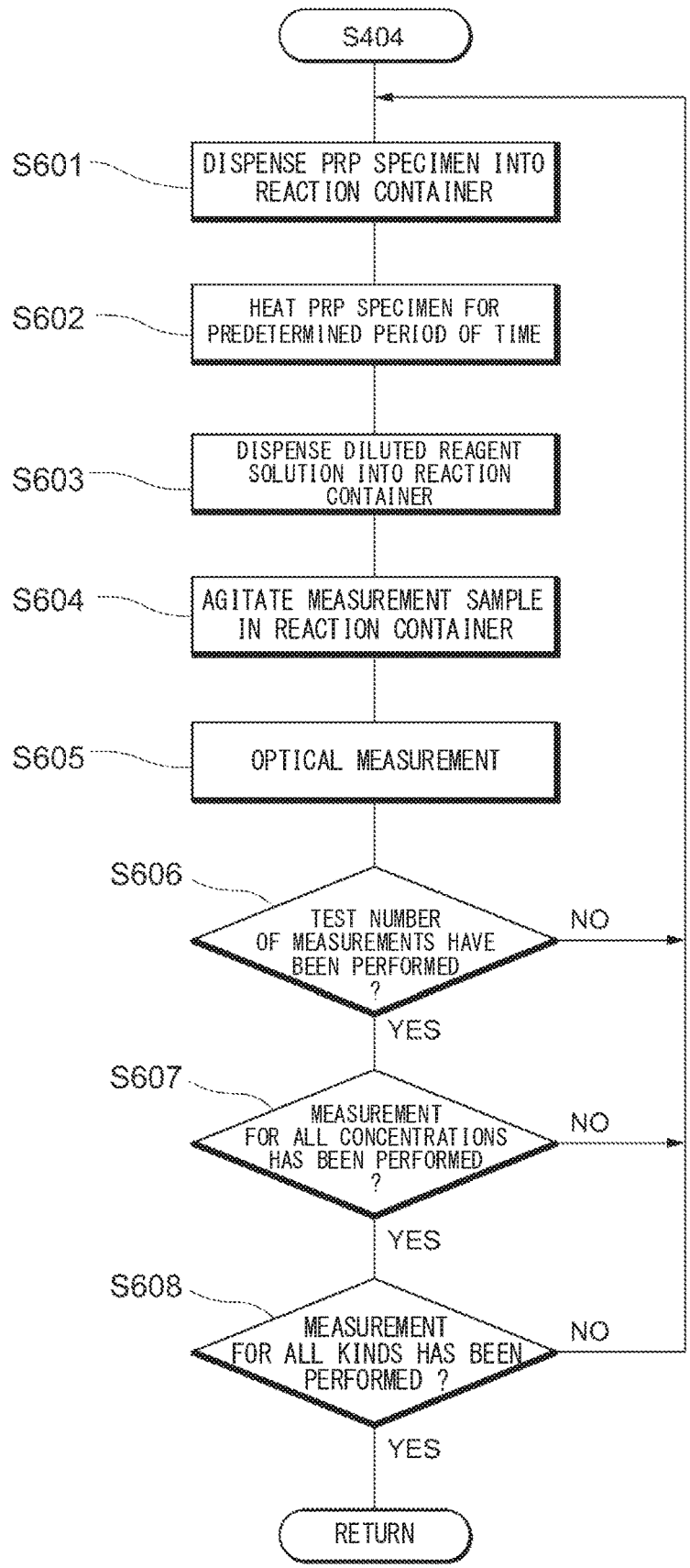
FIG. 23 is a flow chart showing the specimen measurement method according to the embodiment.

In step S404 in FIG. 21, the controller 210 causes the measurement sample preparation unit 12 to prepare a measurement sample of the PRP specimen, and causes the measurement unit 13 to measure the measurement sample of the PRP specimen. Specifically, in step S601 in FIG. 23, the controller 210 causes the first dispenser 150a to suction a predetermined amount $V_S$ of the PRP specimen, from the specimen container 104 that has been determined to contain the PRP specimen, and dispense the PRP specimen into the reaction container 108 having the agitator therein in advance. In step S602, the controller 210 causes the holding mechanism 170 to transfer the reaction container 108 that stores the PRP specimen, onto the heating table 190. The controller 210 causes the heating table 190 to heat the reaction container 108 that stores the PRP specimen, at a predetermined temperature, for a predetermined period of time.

In step S603, the controller 210 causes the second dispenser 120a to suction a predetermined amount of the diluted reagent solution corresponding to the set kind of the platelet-aggregating reagent and the set predetermined concentration of the platelet-aggregating reagent, from the diluted reagent solution container 60, and dispense the predetermined amount $V_1$ of the diluted reagent solution into the reaction container 108 that stores the PRP specimen such that the dilution rate of the platelet-aggregating reagent is the predetermined dilution rate D, to prepare the measurement sample that contains the predetermined concentration of the platelet-aggregating reagent and the PRP specimen. In step S604, the controller 210 causes the holding mechanism 175 to transfer the reaction container 108 that stores the measurement sample to the container placement portion 131 of the measurement unit 13. The controller 210 causes the container placement portion 131 to rotate the agitator in the reaction container 108 and agitate the measurement sample.

In step S605, the controller 210 causes the measurement unit 13 to measure temporal change of an absorbance or a transmittance of the measurement sample that contains the predetermined concentration of the platelet-aggregating reagent and the PRP specimen in the reaction container 108 for a predetermined period of time while the measurement sample is agitated. The controller 210 causes the storage device to store the temporal change, of the absorbance or the transmittance of the measurement sample, which has been measured by the measurement unit 13.

In step S606, the controller 210 determines whether or not preparation and optical measurement of the measurement sample have been repeated according to the set test number. When the test number has not reached the set test number, the process is returned to step S601. When the test number has reached the set test number, the process proceeds to step S607. In step S607, the controller 210 determines whether or not the preparation and measurement of the measurement sample have been performed for all of the plurality of predetermined concentrations of the platelet-aggregating reagent in the measurement sample. When the preparation and the measurement of the measurement sample have not been performed for all of the plurality of predetermined concentrations of the platelet-aggregating reagent in the measurement sample, the process is returned to step S601. When the preparation and the measurement of the measurement sample have been performed for all of the plurality of predetermined concentrations of the platelet-aggregating reagent in the measurement sample, the process proceeds to step S608.

In step S608, the controller 210 determines whether or not the preparation and the measurement of the measurement sample have been performed for all of the plurality of kinds of the platelet-aggregating reagents. When the preparation and the measurement of the measurement sample have not been performed for all of the plurality of kinds of the platelet-aggregating reagents, the process is returned to step S601. When the preparation and the measurement of the measurement sample have been performed for all of the plurality of kinds of the platelet-aggregating reagents, the process proceeds to step S405 in FIG. 21.

When the measurement unit 13 has measured the absorbance, the controller 210 of the specimen measurement apparatus 200 operates to transmit the temporal change of the absorbance or the transmittance stored in the storage device, via the communication units 209, 212, to the storage device of the controller 213 of the analyzer 140 in step S405. The controller 213 of the analyzer 140 calculates the maximum aggregation rate from the greatest change amount of the absorbance which is caused by the platelet aggregation reaction for each of the set kind of the platelet-aggregating reagent and the set predetermined concentration of the platelet-aggregating reagent, when the aggregation rate is 0% for the absorbance obtained immediately after the diluted reagent solution is added to the PRP specimen, and the aggregation rate is 100% for the absorbance of the PPP specimen. Specifically, the controller 213 of the analyzer 140 calculates a maximum aggregation rate A (%) by using the following equation (5).

$$A=(OD_{PRPIni}-OD_{PRPmin})/(OD_{PRPIni}-OD_{PPP})\times 100 \quad (5)$$

where $OD_{PRPIni}$ represents an absorbance obtained immediately after the diluted reagent solution is added to the PRP specimen, $OD_{PRPmin}$ represents the lowest absorbance of the measurement sample that contains the PRP specimen to which the diluted reagent solution has been added, and $OD_{PPP}$ represents an absorbance of the PPP specimen. The absorbance and the transmittance are inversely proportional to each other. Therefore, the maximum aggregation rate may be calculated based on the transmittance. The controller 213 of the analyzer 140 causes the storage device to store the calculated maximum aggregation rate.

In step S406, the controller 213 of the analyzer 140 causes the display unit 230 to display a waveform graph of temporal change of the absorbance or the transmittance of the measurement sample, the maximum aggregation rate, and the like for each of the set kinds of the platelet-aggregating reagents and the set predetermined concentrations of the platelet-aggregating reagents, and the method ends.

In the specimen measurement apparatus and the specimen measurement method described above, a diluent of a platelet-aggregating reagent can be automatically prepared according to a predetermined concentration of the platelet-aggregating reagent in a measurement sample. Furthermore, the required amounts of the platelet-aggregating reagent and the diluent can be automatically calculated according to the test number and the predetermined concentration of the platelet-aggregating reagent in the measurement sample as inputted or selected by the user. Therefore, the platelet aggregation test can be efficiently performed. The accuracy of the concentration of a diluent of a platelet-aggregating reagent can be maintained at a high level since the diluent of the platelet-aggregating reagent is automatically prepared.

The present disclosure has been described above according to the embodiment. However, it is to be understood that the description and the drawing which form a part of the disclosure are not restrictive. Various other embodiments, examples, and applied techniques are obvious to a person skill in the art from the present disclosure. For example, an exemplary case where, in step S101 in FIG. 9, the display unit 230 displays the test number input screen 802 that includes the combinations 702 each including the preset kind of a platelet-aggregating reagent and the preset predetermined concentration of the platelet-aggregating reagent in a measurement sample as shown in FIG. 11, is described. However, the controller 210 may receive an input for setting a kind of a platelet-aggregating reagent from a user through the input unit 231. Furthermore, the controller 210 may receive an input for setting a predetermined concentration of the platelet-aggregating reagent in a measurement sample from a user through the input unit 231.

In the above-described embodiment, an exemplary case where the test number is received in step S102 in FIG. 9, is described. However, combinations each including the preset kind of a platelet-aggregating reagent, the preset predetermined concentration of the platelet-aggregating reagent in a measurement sample, and the preset test number may be displayed in advance on the screen shown in FIG. 11. In this case, the user may select any of the combinations each including the preset kind of a platelet-aggregating reagent, the preset predetermined concentration of the platelet-aggregating reagent in a measurement sample, and the preset test number without inputting the test number. In this case, the controller 210 causes the storage device to store the selected combination. Thereafter, in step S103, the controller 210 performs calculation necessary for automatically preparing the diluted reagent solution based on the test number in the selected combination.

In the above-described embodiment, an exemplary case where, in step S104 to step S106, a user places the reagent container 90, the diluent container 50, and the diluted reagent solution container 60 in the reagent preparation table 180 based on the result of calculation of the required amount of the platelet-aggregating reagent and the required amount of the diluent, is described. However, before step S101, the user may place the reagent container 90, the diluent container 50, and the diluted reagent solution container 60 in the reagent preparation table 180 in advance, and the controller 210 may perform, in step S103, calculation necessary for automatically preparing the diluted reagent solution, and, thereafter, the controller 210 may operate to automatically start reading the reagent information and measuring the storage amount (remaining amount) of the platelet-aggregating reagent and the storage amount (remaining amount) of the diluent in steps S107 and S108 without receiving an instruction from the user by omitting step S104 to step S106. Furthermore, steps S110 and S111 may be omitted, and the controller 210 may start automatic preparation of the diluted reagent solution in step S112 without receiving an instruction from the user.

Thus, it is to be understood that the present disclosure also includes various embodiments and the like other than those described herein.

What is claimed is:

1. A specimen measurement method for measuring platelet aggregation of a specimen, the specimen measurement method comprising:
providing a specimen obtained by centrifuging blood;
displaying a plurality of preset combinations on a display,
wherein each preset combination includes a kind of a platelet-aggregating reagent and a predetermined concentration of the platelet-aggregating reagent;

receiving, by a controller, a selection of at least one preset combination of the plurality of preset combinations from among the plurality of preset combinations displayed on the display;

receiving, by the controller via an input box displayed on the display, a test number that:
  corresponds to the received at least one preset combination of the kind of the platelet-aggregating reagent and the predetermined concentration of the platelet-aggregating reagent;
  represents a number of times a measurement sample will be prepared and measured under a same condition;

calculating a required amount of diluted reagent solution for the received at least one present combination using the received test number as a variable in a linear equation;

automatically preparing a diluted reagent solution that contains a platelet-aggregating reagent diluted with a diluent based on the received at least one preset combination and the received test number, wherein the automatically preparing the diluted reagent solution comprises suctioning the diluent by a dispensing suction tube of a dispenser, suctioning the platelet-aggregating reagent by the dispensing suction tube of the dispenser, and dispensing the diluent and the platelet-aggregating reagent from the dispenser into a diluted reagent solution container for storing the diluted reagent solution;

preparing the measurement sample that contains a predetermined concentration of the platelet-aggregating reagent, from the diluted reagent solution and the specimen; and performing optical measurement of the measurement sample.

2. The specimen measurement method of claim 1, further comprising determining a required amount of the platelet-aggregating reagent and a required amount of the diluent, based on the predetermined concentration of the platelet-aggregating reagent in the measurement sample.

3. The specimen measurement method of claim 2, wherein the automatically preparing the diluted reagent solution comprises substituting a minimum amount of the diluent which can be suctioned by a dispenser, for the required amount of the diluent, when the required amount of the diluent is less than the minimum amount of the diluent which can be suctioned by the dispenser.

4. The specimen measurement method of claim 1, further comprising receiving setting of the predetermined concentration of the platelet-aggregating reagent in the measurement sample, wherein
  the automatically preparing the diluted reagent solution comprises preparing the diluted reagent solution based on the received setting of the predetermined concentration of the platelet-aggregating reagent.

5. The specimen measurement method of claim 4, further comprising determining a required amount of the platelet-aggregating reagent and a required amount of the diluent, based on the received setting of the predetermined concentration of the platelet-aggregating reagent.

6. The specimen measurement method of claim 1, further comprising receiving a kind of the platelet-aggregating reagent, wherein
  the automatically preparing the diluted reagent solution comprises preparing the diluted reagent solution according to the received kind of the platelet-aggregating reagent and the diluent.

7. The specimen measurement method of claim 1, further comprising receiving setting of a test number by which the preparing the measurement sample and the performing optical measurement of the measurement sample are repeated.

8. The specimen measurement method of claim 7, further comprising determining a required amount of the platelet-aggregating reagent and a required amount of the diluent, based on the received test number and the predetermined concentration of the platelet-aggregating reagent in the measurement sample.

9. The specimen measurement method of claim 1, further comprising reading a preset test number by which the preparing the measurement sample and the performing optical measurement of the measurement sample are repeated.

10. The specimen measurement method of claim 1, wherein the preparing the measurement sample comprises preparing a platelet-rich plasma (PRP) measurement sample containing the predetermined concentration of the platelet-aggregating reagent, from the diluted reagent solution and a platelet-rich plasma (PRP) specimen, and preparing a platelet-poor plasma (PPP) measurement sample from the diluent and a platelet-poor plasma (PPP) specimen, and
  the performing optical measurement comprises performing optical measurement of the platelet-rich plasma (PRP) measurement sample and the platelet-poor plasma (PPP) measurement sample.

11. The specimen measurement method of claim 10, further comprising analyzing platelet aggregation of the specimen based on a result of the optical measurement.

12. The specimen measurement method of claim 11, wherein the analyzing platelet aggregation comprises calculating a platelet aggregation rate based on an absorbance or a transmittance of each of the PRP measurement sample and the PPP measurement sample.

13. The specimen measurement method of claim 1, wherein the automatically preparing the diluted reagent solution comprises dispensing the diluent and the platelet-aggregating reagent into a diluted reagent solution container divisionally by a plurality of number of times.

14. The specimen measurement method of claim 1, wherein at least one of a kind of the platelet-aggregating reagent and the predetermined concentration of the platelet-aggregating reagent in the measurement sample is preset for at least one of detection of dysfunction of platelet aggregation and monitoring of a drug efficacy of an antiplatelet aggregation drug.

15. The specimen measurement method of claim 1, wherein the platelet-aggregating reagent is at least one selected from the group consisting of adenosine diphosphate (ADP), collagen, epinephrine, arachidonic acid, ristocetin, and protease-activated receptor 1-activating peptide (PAR1-AP).

16. The specimen measurement method of claim 1, wherein the performing optical measurement of the measurement sample comprises measuring temporal change of an absorbance or a transmittance.

17. The specimen measurement method of claim 1, wherein the specimen is a platelet-rich plasma specimen.

18. The specimen measurement method of claim 1, further comprising selecting a number of samples to be produced for each selected preset combination, wherein the selected at least one preset combination and the selected number of samples are simultaneously displayed on a single display screen.

19. A specimen measurement apparatus for measuring platelet aggregation of a specimen, the specimen measurement apparatus comprising:
- a controller configured to store a plurality of preset combinations, wherein each preset combination includes a kind of a platelet-aggregating reagent and a predetermined concentration of the platelet-aggregating reagent, wherein the controller is configured to receive via user input a selection of at least one preset combination of the plurality of present combinations and a selection of a test number that: a) corresponds to the received at least one preset combination of the kind of the platelet-aggregating reagent and the predetermined concentration of the platelet-aggregating reagent; b) represents a number of times a measurement sample is-will be prepared and measured under a same condition, wherein the controller calculates a required amount of diluted reagent solution for the received at least one preset combination using the received test number as a variable in a linear equation;
- an input unit coupled to the controller, the input unit configured to receive input from a user and transmit the input to the controller;
- a display coupled to the controller for displaying the plurality of preset combinations;
- a diluted reagent solution preparation unit configured to prepare a diluted reagent solution that contains a platelet-aggregating reagent diluted with a diluent based on the received at least one preset combination of the plurality of preset combinations and the received test number, wherein the diluted reagent solution preparation unit is configured to suction the diluent by a dispensing suction tube of a dispenser, and suction the platelet-aggregating reagent by the dispensing suction tube of the dispenser, and dispense the diluent and the platelet-aggregating reagent from the dispenser into a diluted reagent solution container for storing the diluted reagent solution;
- a measurement sample preparation unit configured to prepare the measurement sample that contains a predetermined concentration of the platelet-aggregating reagent, from the diluted reagent solution and the specimen; and
- a measurement unit configured to perform optical measurement of the measurement sample, wherein the specimen is obtained by centrifuging blood.

20. The specimen measurement apparatus of claim 19, wherein the diluted reagent solution preparation unit comprises a reagent preparation table, wherein the reagent preparation table comprises a first table disposed at a center and a second table disposed at an outer circumference of the first table, wherein the first table and the second table are independently rotatable around a rotation shaft.

* * * * *